(12) United States Patent
Foord et al.

(10) Patent No.: US 10,677,724 B2
(45) Date of Patent: Jun. 9, 2020

(54) SAMPLE TESTING APPARATUS AND METHOD

(71) Applicants: Anthony Peter Foord, Worthing (GB); Stuart Lucas Lunt, Watersfield (GB)

(72) Inventors: Anthony Peter Foord, Worthing (GB); Stuart Lucas Lunt, Watersfield (GB)

(73) Assignee: Parker Hannifin Manufacturing (UK) Ltd., Hemel Hempstead, Hertfordshire (GB)

( * ) Notice: Subject to any disclaimer, the term of this patent is extended or adjusted under 35 U.S.C. 154(b) by 0 days.

(21) Appl. No.: 15/956,930

(22) Filed: Apr. 19, 2018

(65) Prior Publication Data

US 2019/0277756 A1    Sep. 12, 2019

Related U.S. Application Data

(63) Continuation of application No. PCT/GB2016/053236, filed on Oct. 18, 2016.

(30) Foreign Application Priority Data

Oct. 19, 2015    (GB) .................................. 1518470.8

(51) Int. Cl.
*G01N 21/03*    (2006.01)
*G01N 21/3577*    (2014.01)
(Continued)

(52) U.S. Cl.
CPC .......... *G01N 21/3577* (2013.01); *G01N 1/12* (2013.01); *G01N 21/0303* (2013.01);
(Continued)

(58) Field of Classification Search
CPC .. G01N 21/3577; G01N 1/12; G01N 33/2847; G01N 33/2876; G01N 21/03
(Continued)

(56) References Cited

U.S. PATENT DOCUMENTS 4,762,798 A * 8/1988 Deutsch ................. G01N 21/75
356/246
4,938,602 A    7/1990 May
(Continued)

FOREIGN PATENT DOCUMENTS

CN    201145668 Y    11/2008
DE    2810117    9/1979
(Continued)

OTHER PUBLICATIONS

International Search Report and Written Opinion for International Application No. PCT/GB2016/053236 dated Jan. 18, 2017.
(Continued)

*Primary Examiner* — Roy M Punnoose
(74) *Attorney, Agent, or Firm* — Christopher H. Hunter

(57) ABSTRACT

A sample testing apparatus is disclosed for use in optical transmission analysis of fluid samples such as oils or engine oils. The apparatus comprises a transmission cell comprising first and second fixed walls (1,2) and a movable window (3) that is moved with respect to the first and second walls in and out of a test region (6). When the movable window (3) is moved into the test region (6) an optical path through a fluid sample in the cell is defined, the optical path through the sample comprising a portion extending through the or each gap ($L_1, L_2$) between a one of the first and second fixed walls (1,2) and the at least a portion of the first movable window (3). Also disclosed are methods of using the sample testing apparatus and methods of performing a measurement for use in optical transmission analysis of a fluid sample.

61 Claims, 6 Drawing Sheets

(51) Int. Cl.
  *G01N 1/12* (2006.01)
  *G01N 33/28* (2006.01)
  *G01N 21/85* (2006.01)
  *G01N 21/15* (2006.01)

(52) U.S. Cl.
  CPC ......... *G01N 21/15* (2013.01); *G01N 21/8507* (2013.01); *G01N 33/2847* (2013.01); *G01N 33/2876* (2013.01); *G01N 2021/0307* (2013.01); *G01N 2201/063* (2013.01)

(58) Field of Classification Search
  USPC .......................................................... 356/70
  See application file for complete search history.

(56) References Cited

U.S. PATENT DOCUMENTS

| | | | |
|---|---|---|---|
| 6,643,021 | B1 | 11/2003 | Kawamura |
| 7,330,262 | B2 * | 2/2008 | Siepmann .............. G01N 21/15 |
| | | | 356/432 |
| 7,826,050 | B2 * | 11/2010 | DiFoggio ........... G01N 21/0303 |
| | | | 356/241.1 |
| 10,036,702 | B2 * | 7/2018 | Ramsteiner ............ G01N 21/31 |
| 2005/0117156 | A1 * | 6/2005 | Siepmann .............. G01N 21/15 |
| | | | 356/436 |
| 2009/0059332 | A1 * | 3/2009 | DiFoggio ........... G01N 21/0303 |
| | | | 359/196.1 |
| 2012/0038925 | A1 * | 2/2012 | Gahr ...................... G01N 21/15 |
| | | | 356/440 |
| 2014/0375997 | A1 * | 12/2014 | Gilan ................ G01N 21/0303 |
| | | | 356/440 |

FOREIGN PATENT DOCUMENTS

| | | | | |
|---|---|---|---|---|
| EP | 0 039088 | | 4/1981 | |
| EP | 0039088 | A1 * | 11/1981 | ........... G01N 21/255 |
| JP | 55027964 | | 2/1980 | |
| JP | 55027964 | A * | 2/1980 | ......... G01N 21/0303 |
| JP | S5529780 | | 3/1980 | |
| JP | S56124037 | | 9/1981 | |
| JP | 08219981 | | 8/1996 | |
| JP | 2006-194775 | | 7/2006 | |
| JP | 2006194775 | A * | 7/2006 | |
| JP | 2006226948 | | 10/2006 | |
| JP | 2008145411 | | 6/2008 | |
| JP | 201091921 | | 4/2010 | |
| JP | 2014222187 | | 11/2014 | |
| WO | WO-2009032981 | A1 * | 3/2009 | ......... G01N 21/0303 |

OTHER PUBLICATIONS

Combined Search and Examination Report for GB1617640.6 dated Apr. 18, 2017.
Search Report for GB1518470.8 dated Apr. 13, 2016.
Communication pursuant to Article 94(3) EPC for European Application No. 16 787 521.0 dated Jun. 13, 2019.

* cited by examiner

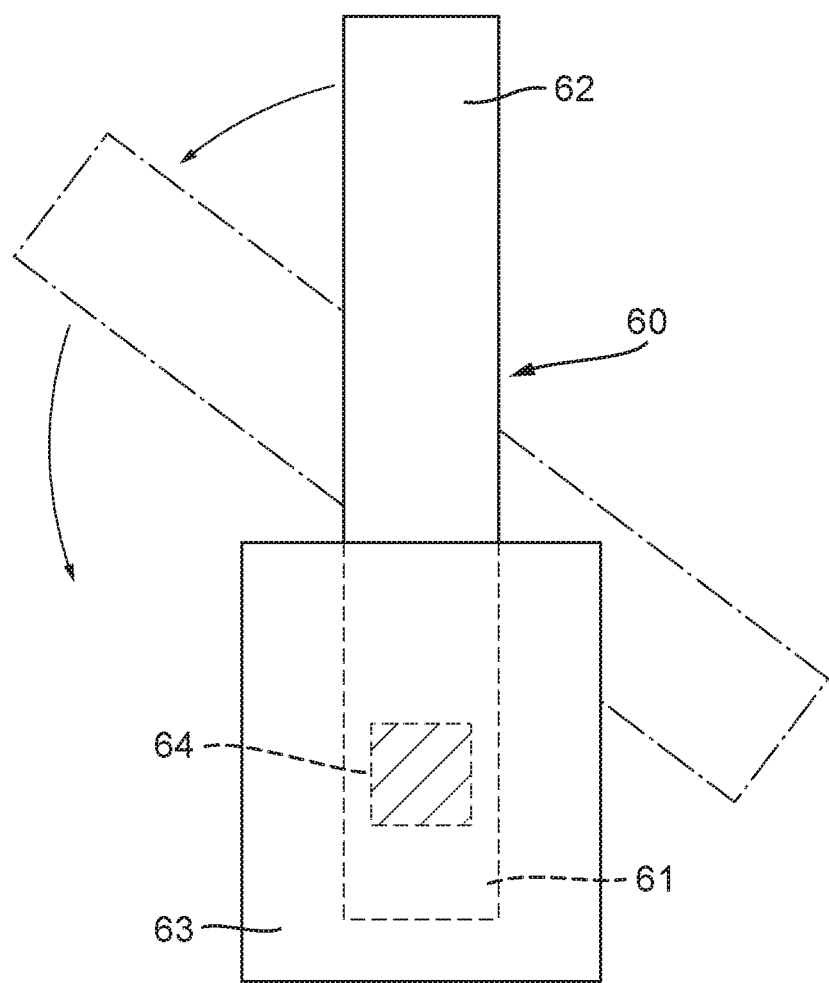

SAMPLE TESTING APPARATUS AND METHOD

This application is a Continuation application pursuant to 35 U.S.C. § 120 of PCT/GB2016/053236 filed on Oct. 18, 2016, which claims the benefit of G.B Application No. 1518470.8 filed Oct. 19, 2015, the contents of both of which are incorporated herein by reference.

FIELD OF THE INVENTION

The present invention relates to a sample testing apparatus for use in optical transmission analysis, and a method of using the apparatus. The present invention is particularly, although not exclusively, concerned with optical transmission analysis of liquids.

BACKGROUND

Optical transmission analysis may be performed to determine the presence and/or concentration of a substance in a sample based on the interaction of electromagnetic radiation with the sample. In practice, optical transmission analysis may be performed by consideration of a ratio of the intensity of the radiation detected after passing through the sample to the initial intensity of the radiation incident on the sample i.e. the transmittance through the sample. Typically, the analysis considers the absorbance of the sample, which may be determined from the transmittance, and is proportional to the concentration of the absorbing substance, and the optical path length traveled by the radiation through the sample.

For a given wavelength of incident radiation, the concentration of a substance may be determined based on the initial power ($I_o$) of the radiation entering a transmission cell containing the substance, and the power of the radiation detected after passing through the cell ($I_T$), where the radiation has traveled along a path length L through the sample, according to the following relationship;

$$I_T = I_o \cdot e^{-\alpha \cdot c \cdot L}$$

where c is the concentration of the absorbing substance, $\alpha$ is an absorption coefficient and L is the path length. This is commonly referred to as the Beer-Lambert law.

Taking the log of the detected power gives the convenient linear relationship:

$$\log(I_T) = \log(I_O) - \alpha \cdot c \cdot L$$

As may be seen from the relationship above, the optical path length through the sample is a key parameter, controlling the degree to which radiation is absorbed by the sample. The extent to which radiation is absorbed also depends upon the nature of the test sample, and the wavelength of the radiation. For example, liquid samples tend to absorb radiation relatively strongly in the infrared region, which is most commonly used in optical analysis of samples, and therefore a relatively small path length is required, for example, commonly used path lengths being in the order of 50-250 micrometers. While the present invention is not limited to the use of infrared radiation, as this is the most commonly used wavelength, which is associated with a convenient path length, it is important to be able to provide an apparatus that is particularly effective for use with such a wavelength range.

Various types of apparatus may be used to perform measurements on samples for use in carrying out optical analysis of the sample based on transmission. One technique, which is applicable to measuring liquid samples, is based on Attenuated Total Reflectance (ATR). In ATR based methods, a liquid sample to be tested is placed in contact with a transparent guide material of higher refractive index. A beam of electromagnetic radiation, typically infrared radiation, is caused to pass through the transparent material, and reflect from the interface of the transparent material which contacts the sample. This process results in an evanescent wave extending a small distance into the test liquid, which is subject to absorption. The effective path length is determined by the angle of reflection, the wavelength of the radiation, and the refractive indices of the test liquid and guide material. In general, such techniques are only appropriate for a limited number of substances, which have strong absorption properties, as in practice the path length that may be defined may be limited to only a few micrometers.

Typically, in order to perform transmission analysis on a liquid sample, the sample is held in a transmission cell bounded by windows transparent to electromagnetic radiation of the wavelength to be used in testing, enabling radiation to pass through one of the windows from a source, and be detected on the other side of the cell after passing through the opposite window. The transmission cell is constructed to provide a well-defined path length through the sample. Transmission cells provide a convenient way to provide a suitable, repeatable and well defined path length through a liquid sample. Transmission cells may be used for online testing, in which a sample liquid is caused to flow through the cell, or for testing of extracted samples.

Difficulties may arise in cleaning the cell after a test, and before testing of a new sample. This may be the case in particular where the path lengths are of the small dimensions often required for liquid analysis e.g. of the order of no more than a few hundred micrometres. Problems with cleaning are exacerbated in the case of viscous or dirty fluids, such as lubricating oils, and the cleaning process may take a considerable amount of time, often greater than the time required to perform a measurement. It is important to ensure that the cell is thoroughly cleaned, as even a small amount of contamination from a previous test may significantly affect a subsequent measurement, especially where small path lengths are involved. There may also be difficulties in introducing the fluid to be tested to the cell due to the small dimensions.

SUMMARY

The present invention seeks to provide an improved apparatus for use in optical transmission analysis of fluid samples, particularly, although not exclusively of liquids, which may address at least some of these problems.

In accordance with a first aspect of the invention there is provided a sample testing apparatus for use in optical transmission analysis of a fluid sample, the apparatus comprising;

a transmission cell comprising first and second walls fixed in a spaced relationship relative to one another to define a space therebetween for receiving a fluid sample in use, at least the first wall being associated with a window, wherein electromagnetic radiation may be introduced through the window into the transmission cell in use for detection after passing through the sample;

the apparatus further comprising a first movable window, the first movable window being movable with respect to the first and second fixed walls, wherein the apparatus is operable to cause the first movable window to move with respect to the first and second fixed walls to move at least a portion of the first movable window into and out of a test region of the transmission cell, the test region being a region between the first and second fixed walls in the optical path of electromagnetic radiation introduced through the first fixed window into the transmission cell for passing through a fluid sample located in the space between the first and second fixed walls prior to detection in use;

wherein, when the at least a portion of the first movable window is located in the test region, a gap is defined between the at least a portion of the first movable window and one or both of the first and second fixed walls in the test region of the cell, such that an optical path is defined through a fluid sample in the cell for electromagnetic radiation introduced through the window associated with the first wall, the optical path through the sample comprising a portion extending through the or each gap between a one of the first and second fixed walls and the at least a portion of the first movable window.

In accordance with the invention, therefore, a transmission sample testing apparatus is provided having a transmission cell comprising first and second fixed walls, of which at least the first of which walls comprises a window. The window associated with the first fixed wall may be referred to as the first fixed window. The apparatus further comprises a first movable window having at least a portion that is movable into and out of a test region in a sample receiving space defined between the first and second fixed walls for sample testing. The apparatus is operable to move the first movable window so as to move the at least a portion of the first movable window into and out of the test region of the transmission cell. A gap is defined between the at least a portion of the first movable window and one or both of the first and second walls in at least the test region of the cell. In use, when electromagnetic radiation is introduced through the window associated with the first fixed wall, for detection after passing through the sample, an optical path traveled by the radiation through the sample thus includes portion(s) which extend through the or each gap between a one of the fixed walls and the at least a portion of the first movable window. It will be appreciated that the first and second walls are located in a fixed relationship relative to one another, and the first movable window (and, in further embodiments, any further movable window) is movable relative to the first and second fixed walls into and out of the test region in the space defined therebetween.

It has been found that the movement of the first (or any further) movable window so as to move at least a portion thereof into and out of a test region of the transmission cell e.g. so as to move within the fluid disposed in the transmission cell in use, has the effect of helping to clean the sample contacting surfaces of the cell e.g. the first and second fixed walls and the surfaces of the movable window. This may reduce the need to carry out a specific cleaning step e.g. by immersing the transmission cell into a cleaning fluid e.g. solvent. Rather than needing to carry out specific cleaning after every measurement taken using the apparatus, this may only be necessary after a series of measurements have been taken. When it is necessary to perform specific cleaning, this may be readily carried out by introducing a suitable cleaning fluid to the transmission cell, and moving the first (or further) movable window into and out of the test region one or more times. Furthermore, movement of the movable window to move the at least a portion thereof into and out of the test region may drive the exchange of fluid in the transmission cell. Thus, moving the at least a portion of the movable window out of the test region and then back into the test region after one measurement has been taken and prior to taking a further measurement may renew the fluid sample in the transmission cell. The movement of fluid caused by movement of the first (or further movable) window may also provide some cleaning effect, helping to remove and dilute traces of the previously tested sample.

The present invention provides advantages whether the apparatus is used for testing of an extracted sample, or online testing. By facilitating ease of cleaning, the apparatus may advantageously be used as a portable field instrument. Conventional liquid transmission cell apparatus tends to be more appropriate for use in the laboratory, when it may be possible to spend longer periods disassembling and cleaning the apparatus between measurements. In contrast, in the field, it is important to minimise the time spent on cleaning, and ensure that cleaning may be performed in a simple a manner as possible. In the context of online or flow testing, the apparatus of the present invention may effectively clean itself as it is operated, with the or each movable window helping to promote movement of process fluid into and out of the cell, providing a cleaning effect as it does so. This may reduce the need to remove the apparatus from the system for specific cleaning. If additional cleaning is required, the or a movable window may be operated to move the at least a portion thereof into and out of the test region a few times. This may be achieved without needing to demount the apparatus, or disassemble the transmission cell.

Movement of the first movable window (or any further movable window) into the or a test region may act to displace fluid from inside the transmission cell or draw fluid into the transmission cell. Similarly, movement of the first movable window (or any further movable window) out of the or a test region may act to displace fluid from the transmission cell or draw fluid into the transmission cell. Whether fluid is displaced from or drawn into the transmission cell i.e. the sample receiving space, will depend upon the direction of movement of the window into or out of the test region. Typically, movement of the first movable window into the test region acts to displace fluid from inside the transmission cell. In this way, movement of a movable window may act to drive exchange of fluid within the cell.

The (or a) test region as referred to herein is a region of the transmission cell through which electromagnetic radiation introduced into the cell through the window associated with the first wall (e.g. a beam of radiation) travels in use prior to being detected. Such a region will be in alignment with at least a portion of the window associated with the first fixed wall through which radiation passes from a source, and is also in alignment with a region over which a detector is operable to detect radiation after it has traveled through the sample. The region over which the detector is operable may comprise at least a portion of the window associated with the first wall or, preferably, at least a portion of a window associated with the second wall (i.e. a second fixed window). The test region may be a predefined region. The test region may be an extended region e.g. where the source generates radiation extending over an extended region, and the detector is operable to detect radiation over an extended region, or may be defined by a particular line along which the radiation must pass between the source and detector. An extended region may extend over (only) a portion of the height and width of the cell. The test region may be defined by the path traveled by a beam of radiation between a source and a detector of the apparatus. The test region extends over only a portion of the volume of the transmission cell. For example, the height and width of the test region may correspond to the diameter of a beam of electromagnetic radiation introduced into the cell. The height and/or width of the test region may be less than 15 mm, or less than 10 mm, or less than 5 mm. The test region may extend over no more than 20%, or no more than 10% of the height of the cell. The test region may be located at any desired location in the transmission cell, e.g. at a centre thereof. As mentioned below, it is envisaged that the transmission cell might include more than one test region. In such cases, each may be defined in the above manner. However, preferably a single test region is provided i.e. "the" test region.

The apparatus preferably further comprises a source of electromagnetic radiation arranged to introduce electromagnetic radiation into the transmission cell through the window associated with the first fixed wall in use. The source of electromagnetic radiation may be located on a side of the window associated with the first fixed wall that is opposite that facing the space in which sample fluid is received in use. The source is preferably located behind the first fixed wall i.e. on a side of the wall opposite to that facing the space in which sample fluid is received in use. The source of electromagnetic radiation is suitably fluidly sealed from the fluid receiving space. The window associated with the first wall may seal the source from fluid in the transmission cell in use.

The source of electromagnetic radiation may be of any suitable type to provide radiation of the wavelength or wavelengths desired to be used in the desired sample testing. The source is preferably a source of infrared radiation. Whatever the type of electromagnetic radiation produced, the source may be operable to provide radiation at more than one wavelength e.g. over a range of wavelengths, which may be a continuous range, or may be operable to provide radiation of only a single wavelength. The source may be a source of broadband radiation. The source may be able to provide radiation over a relatively narrow range or a broad range of wavelengths. The source may be operable to selectively provide radiation at more than one wavelength in a given range. The method of the present invention may comprise introducing electromagnetic radiation of a given wavelength or wavelengths into the transmission cell. Preferably the method comprises introducing infrared electromagnetic radiation into the cell.

The source may be of any suitable type. For example, the source may be of any type used in a spectrometer. The source may be able to output radiation over a range of wavelengths, or may be able to output only a narrow range of wavelengths of radiation, or even a single wavelength of radiation. The source may be able to selectively output radiation at different wavelengths in a given range. One type of source may comprise means for generating electromagnetic radiation, and an optical filter(s) to select the relevant wavelength for introduction into the transmission cell. It is also envisaged that the window associated with the first wall may act as an optical filter for the source. The source may be a thermal or quantum source of electromagnetic radiation e.g. infrared radiation. In preferred embodiments, the source is a thermal source of radiation, most preferably infrared radiation. Such a source will provide broadband radiation. The source incorporates those components required to generate electromagnetic radiation of a desired wavelength or wavelengths for use with the apparatus, and introduce the radiation through the window associated with the first fixed wall. In some simple embodiments, the control of the wavelengths used in testing may be achieved by arranging the detector to detect only specific wavelengths. The source may then be arranged to output radiation over a wider range of wavelengths.

The source defines a region over which electromagnetic radiation is introduced into the cell through the window associated with the first wall. The source may be arranged to output radiation in the form of a beam. The diameter of beam may be of any desired size. The beam may be, for example, of less than 15 mm diameter, or less than 10 mm diameter, or less than 5 mm diameter.

The apparatus preferably further comprises a detector for detecting electromagnetic radiation after it has traveled through the test region of the transmission cell i.e. after it has passed along the optical path between the first and second fixed walls through the sample. The detector defines a detection region in which it is operable to detect radiation after passing through the sample. The detector is suitably fluidly sealed from the fluid receiving space. The detector may be located behind at least one window associated with the first or second fixed wall. Where the window is a window associated with the first fixed wall, the window may be the (first) fixed window through which radiation is introduced into the cell, or another fixed window associated with the wall. The wall and/or window may seal the detector from the fluid receiving space. Where the detector is located behind at least one window associated with the first or second fixed wall, the detector may be located behind a single window associated with the applicable fixed wall, or a set of a plurality of windows e.g. a cluster of windows may be provided.

The detector is preferably located on an opposite side of the transmission cell to the source of electromagnetic radiation. The detector may be located on a side of the second wall opposite that facing the space in which sample fluid is received in use. In such embodiments, the second fixed wall is associated with at least one window, and may be associated with a set of a plurality of windows behind which the detector is located. In preferred embodiments the second fixed wall is associated with a single fixed window behind which the detector is located. The wall and the at least one window associated therewith may seal the detector from fluid in the transmission cell. However, it is envisaged that in other embodiments the detector may be located behind the or a window of the first fixed wall. The second fixed wall then comprises a mirror for reflecting radiation back towards the window associated with the first fixed wall for detection.

The detector may be of any suitable type, and may be operable to detect radiation of one or more given wavelengths e.g. over a wavelength range, or one or more specific wavelengths. In some preferred embodiments the detector is operable to detect radiation at a plurality of specific wavelengths. The detector may comprise an array of detector units, each arranged to detect a given wavelength of radiation. For example, each unit may be arranged to receive radiation through a different window associated with the fixed wall (e.g. the second fixed wall) behind which the detector is located as described below. Alternatively, or additionally, the detector may comprise one or more optical filters, each corresponding to a wavelength of radiation that it is desired to detect. Each optical filter may be associated with a given detector unit of the detector. In these embodiments the source may output radiation over a range of wavelengths, with the detector defining the or each wavelength that is to be detected in use. In some embodiments in which the detector is located behind a set of a plurality of windows associated with the applicable fixed wall e.g. the second fixed wall, it is envisaged that each window may comprise an optical filter allowing radiation of a given wavelength to pass therethrough and reach the detector e.g. a given detector unit thereof. Each window may provide an optical filter allowing radiation of a different wavelength to pass therethrough to reach the detector. However, in preferred embodiments, the detector is located behind a single window associated with the applicable fixed wall of the transmission cell. The detector may then comprise a plurality of windows, e.g. each associated with a detector unit of the detector, each window providing an optical filter to permit radiation of a given wavelength to pass therethrough. In more complex arrangements, the detector may be arranged in other manners such that it can be set to detect radiation of particular wavelength(s).

The region over which the electromagnetic radiation is introduced into the cell and the detection region may define the test region of the cell. The test region may correspond to the region of the cell between the first and second fixed walls in which the detection region overlaps with the region over which electromagnetic radiation is introduced to the cell. The detection region corresponds to the region over which the detector is operable to detect electromagnetic radiation introduced into the cell through the first fixed window. The detection region may be defined by a region of one of the fixed walls, preferably the second fixed wall, and most preferably by a region of a second fixed window that provides the wall. Any further test region may be defined in a similar manner by a respective detection region and region over which electromagnetic radiation is introduced into the cell.

The source and detector preferably form part of a sample testing unit comprising the sample testing apparatus. The source and detector preferably form an integral part of the sample testing apparatus or unit. The source and detector may then be fixedly mounted with respect to the transmission cell e.g. within a housing of the sample testing unit. Preferably the source and detector are located within a housing of the sample testing unit. However, it is envisaged that the transmission cell of the sample testing apparatus may be removably mountable with respect to the source and detector. For example, the cell may be received in a space between the source and detector. The fixed walls of the transmission cell may then separate the cell from the source and detector. The detector and source would then need to be suitably fluidly sealed from the sample when received in the space.

References to a wall being associated with a window herein encompass the wall comprising the window in any suitable manner. The wall may include the window e.g. the window may be a discrete window in the wall, or, in preferred embodiments, the wall may be defined by the window.

In accordance with the invention in any of its aspects or embodiments, the first fixed wall is associated with a window. The wall is preferably associated with a single window, but it is envisaged that multiple windows could be provided e.g. where both a detector and source are located behind the wall. The first fixed wall comprises the window. The wall may include or be provided by the window. The window may be a discrete window extending over a portion of the wall. However, in preferred embodiments the first fixed wall is provided by the window. In these embodiments a surface of the window defines the wall. In some preferred embodiments the transmission cell includes a single window on one side thereof which provides the first fixed wall. In these preferred embodiments, the boundary of the cell on one side is defined by the window.

The second fixed wall may or may not be associated with a window. In embodiments in which the detector is located on the same side of the transmission cell as the source, it is not necessary for radiation to pass through the second fixed wall, and it need not comprise a window. The second fixed wall may then comprise a mirror. The mirror may be provided by a coating on the wall. In these embodiments the wall could still be provided by a window material, although the mirror will prevent radiation from passing therethrough. However, in preferred embodiments in which the detector is located behind the second fixed wall in use, the wall preferably is associated with a window, most preferably a single window, although it may be associated with a plurality of windows. As discussed above, this may enable radiation to pass through the wall to reach the detector. In preferred embodiments the second fixed wall is associated with a single window. The wall is then preferably provided by the window. A surface of the window may provide the wall. The boundary of the cell on one side may then be defined by the window. However, in other embodiments, the wall may comprise one or more discrete windows therein e.g. a cluster of windows. Each window may be arranged to pass a particular wavelength of radiation i.e. to act as an optical filter for providing radiation of a given wavelength to the detector.

In preferred embodiments the transmission cell is bounded by first and second windows on either side thereof, the windows providing respectively the first and second fixed walls. Preferably a single window bounds the transmission cell on each side thereof. Such arrangements may facilitate construction of the cell. In these preferred embodiments, any reference to the first or second fixed wall may be replaced by a reference to the first or second fixed window to the extent they are not mutually exclusive.

In accordance with the invention, when the first, (or, in some preferred embodiments) a further, movable window is located such that at least a portion thereof is in the (or a) test region, a gap is defined between the at least a portion of the movable window and one or both of the first and second fixed walls. Thus a gap is defined between the at least a portion of the movable window and the fixed wall on one or both sides of the movable window in the test region. While it is envisaged that a gap may be present on only one side of the portion of the movable window, i.e. with the portion of the window contacting the fixed wall on the other side thereof, in preferred embodiments, when the at least a portion of the movable window is located in the test region between the first and second fixed walls, in the test region of the cell, a first gap is defined between the window associated with the first fixed wall and the at least a portion of the movable window, and a second gap is defined between the at least a portion of the movable window and the second fixed wall, wherein the optical path defined through the sample between the first and second fixed walls for electromagnetic radiation introduced through the window associated with the first wall in the test region comprises (or consists of) a first portion extending through the first gap (between the window of the first fixed wall and the at least a portion of the movable window), and a second portion extending through the second gap (between the at least a portion of the movable window and the second fixed wall). The electromagnetic radiation may travel along the optical path through the sample between the first and second fixed walls in one direction, or in two opposed directions, depending upon the location of a detector, i.e. whether it is on the same or opposite side of the transmission cell as the source of electromagnetic radiation.

It will be appreciated that the optical path defined through the sample between the first and second fixed walls in the test region (when the at least a portion of the first or further movable window is located in the or a test region) is a predetermined optical path. The length of the optical path through the sample between the first and second fixed walls is predefined. The path length is determined by the thickness of the at least a portion of the movable window located in the test region, and the spacing between the first and second fixed walls in the test region. The optical path through the sample between the first and second fixed walls is given by the difference between the spacing of the first and second fixed walls in the test region and the thickness of the at least a portion of the movable window located in the test region. The relative sizes of the gaps on either side of the movable window and the first and second fixed walls respectively, (or indeed whether gaps are provided on both sides), is not critical, as the path length through the sample is predefined and known, being controlled by the thickness of the at least a portion of the movable window and the spacing between the fixed walls. Thus, it is not necessary that the movable window is precisely aligned in any particular position in the lateral direction i.e. the direction along which the width of the space between the fixed walls is defined. A gap may be small, for example accommodating only a film of fluid.

The (total) optical path through the sample in the test region that is traveled by radiation prior to detection when the at least a portion of the first (or further) movable window is located in the test region may be given by the sum of the lengths of the first and second portions of the path through the sample between the first and second fixed walls where a source and detector are located on opposite sides of the transmission cell, or double the sum of the first and second portions of the path if the source and detector are located on the same side of the transmission cell. In other words, the total optical path traveled may be once or twice the optical path traveled by the radiation through the sample between the first and second fixed walls. The above features are applicable to any movable window when located in the test region e.g. the first, or any further, such as a second movable window, although as mentioned below, it is not essential that gaps are necessarily defined on both sides of any further window. The or each gap is filled with the sample fluid to be tested in use. Thus, an optical path is defined through the sample between the first and second walls of the cell for electromagnetic radiation introduced through the window associated with the first wall, which optical path comprises a portion extending through the or each gap between a one of the first and second walls and the at least a portion of the movable window.

As will be appreciated, the path length traveled by radiation through the sample fluid prior to detection required for a particular application will depend upon the nature of the fluid being tested, and the wavelength of radiation used. While the path length may vary within a wide range depending upon requirements, the apparatus of the present invention is particularly applicable to providing small path lengths, such as are commonly used when testing liquids using infrared radiation. In preferred embodiments the path length is therefore suitable for use in testing a liquid using infrared radiation. Such applications may involve path lengths through the sample prior to detection of up to a few centimetres, for example where it is desired to try to identify small traces of contaminants in a sample. For example, the path length through the sample may be in the range of less than 2 cm. However, more typically path lengths through the sample used in infrared liquid testing are in the order of up to 1000 micrometres, such as less than 500 micrometres, or less than 250 micrometres. The path length through the sample may be e.g. at least 10 micrometres, or at least 50 micrometres. The path length through the sample may be in any of the above ranges, or combinations thereof, although is not limited thereto, and different path lengths may be used depending upon factors such as the nature of the electromagnetic radiation, which is not limited to the use of infrared radiation, the nature of the sample to be tested, and the nature and likely quantity of substances being tested for in the sample. The present invention is particularly useful in providing an apparatus with a small path length through the sample, and which may be easily cleaned despite the small dimensions. In preferred embodiments the total path length through the sample traveled prior detection corresponds to the path length through the sample between the first and second fixed walls i.e. as the cell is traversed in only one direction by the radiation. In preferred embodiments the optical path defined through the sample between the first and second fixed walls is within any of the ranges given above for the path length traveled by radiation prior to detection. It will be appreciated that the use of the movable first (and optionally further) window allows effective cleaning to be provided even where the dimensions of the liquid transmission cell are so small, and may also help to ensure that fluid effectively enters the space to provide a sample, and subsequently renew a sample after use.

The width of the space defined between the first and second fixed walls of the transmission cell in the (or any further) test region may be of any suitable dimension. This corresponds to the spacing of the walls as measured between their opposed facing surfaces. Preferably the walls are spaced by a constant distance over their height, at least in the test region, and preferably over their entire height. The width of the space defined between the first and second fixed walls is defined by the distance between the first and second walls in the test region i.e. in the region through which radiation travels prior to detection in use, and may be perpendicular to both the first and second walls. The most suitable width will depend upon the path length required to be traveled through the sample by radiation of the wavelength that is to be used in measurement, and the nature of the fluid to be tested. In accordance with the invention, as the first (or a further) movable window is located in the space in the test region during measurement, the path length traveled by radiation through the sample depends additionally on the thickness of the at least a portion of the movable window through which the radiation passes, and hence the width of the gap or gaps defined on one or both sides of the movable window between the movable window and the first and/or second fixed walls. The path length is not solely dictated by the space between the first and second walls in the test region. In some exemplary embodiments the space between the first and second fixed walls in the test region has a width of at least 1 mm, or at least 1.5 mm. The space may have a width of less than 4 mm, or less than 3 mm, or less than 2.5 mm. Such ranges have been found to be suitable when testing a liquid sample e.g. an oil sample using infrared radiation.

A window associated with either of the first or second fixed walls may have a small wedge angle on one or more faces thereof, or may be slightly angled as a whole, to reduce the effect of reflections as known in the art. Such reflections may arise as a result of a difference between the refractive index of the window material and the fluid being analysed on one side of the window, and the air on the opposite side of the window, and can give rise to interference fringes. However, any such wedge angle or angle of inclination should be chosen such that all radiation passing through the test region may be considered to have the same predetermined path length through the sample i.e. such that there is no appreciable difference between the paths traveled by radiation e.g.

a beam of radiation across the test region, and all such radiation may be considered to have the same average nominal path length.

The above features regarding a path length through the sample in the test region defined when at least a portion of a movable window is in the test region, e.g. whether it is defined by gaps on one or both sides of the window, and the other features regarding the path, are applicable to the first movable window when in the test region, and are equally applicable to the at least a portion of any further movable window e.g. the second movable window used in certain preferred embodiments when located in the or a test region. The features are also applicable to a further portion of e.g. the first movable window having first and second portions of differing thickness when located in the or a test region. However, it will be appreciated that for the at least a portion of a further movable window, or portion of the first movable window, it is not essential that a gap is defined on either side thereof when located between the first and second fixed walls, as discussed below.

The first and second fixed walls may be disposed in any suitable manner such that they are fixed in a spaced relationship relative to one another. The first and second walls are in a fixed position relative to the apparatus. As mentioned previously, the first and second fixed walls are provided by first and second windows in preferred embodiments. References to the first and second fixed walls may then be replaced by references to first and second fixed windows in any of the embodiments of the invention. This may provide a more efficient construction for the cell. Furthermore, each window may be formed of the same material. This may help to avoid any differences in thermal expansion between the windows, ensuring that a predetermined path length through a sample may be obtained under different temperature conditions. In general, the windows may be formed of any suitable optical window material that is transparent at the wavelength(s) of interest. For example, suitable optical window materials may include calcium fluoride, sapphire, zinc selenide, fused silica and diamond. However, depending on the application and arrangement of the windows a wide range of other materials may suitably be used.

In other embodiments, one or both walls may include a respective window therein. In such embodiments, a portion of the or each wall will be defined by the respective window. In preferred embodiments the first and second fixed walls respectively fluidly seal a source of electromagnetic radiation and a detector from the interior of the transmission cell.

The first and second walls are fixed relative to one another such that a space is defined therebetween into which fluid is received when the apparatus is used for testing a sample. The space is bounded by the facing surfaces of the first and second walls. The walls have a predetermined spacing. This may be achieved in any suitable manner. In some embodiments one or more spacer is used to maintain a predetermined spacing between the first and second walls. The one or more spacers are preferably selected to have the same or a similar thermal expansion coefficient to the material of the first and second walls. This may help to ensure that the optical path through the sample does not vary significantly with temperature. In preferred embodiments in which the first and second walls are provided by first and second fixed windows, the one or more spacers may be formed of the same material as the windows. In embodiments, the one or more spacers may additionally, or alternatively, comprise a plurality of glass microspheres and a binder material e.g. adhesive.

The first and second walls e.g. windows are mounted in a facing relationship. The walls are preferably spaced from one another over their entire extent. The space between the windows preferably extends over the entire area where the walls face one another. Preferably the spacing between the walls e.g. windows is constant over their extent.

Each wall e.g. window defines a height, a width and a thickness. The thickness is the dimension through the substrate of the wall e.g. window.

The transmission cell comprises, or is defined by the first and second walls, and the space therebetween. The transmission cell may be bounded by the first and second walls and the edges of the space defined therebetween. The first and second walls are each configured to provide a fluid tight seal on their respective side of the transmission cell. Each wall is preferably continuous over its extent. In some embodiments the first and second walls e.g. windows are mounted to the front a source of electromagnetic radiation and a detector respectively.

The apparatus is arranged such that fluid may enter the space between the first and second walls to provide a fluid sample in the transmission cell for testing. Likewise, fluid may leave the space in the same manner e.g. when the transmission cell is removed from a fluid, and/or when a movable window is moved into or out of the space so as to displace fluid. In flow through type embodiments for online testing, the transmission cell may be mounted in the path of a flow of process fluid, so that the fluid may enter and leave the cell. Thus, it will be appreciated that fluid may enter or leave the transmission cell and/or the space between the first and second walls in any of the manners described herein. The transmission cell comprises one or more openings to enable fluid to enter the space. In preferred embodiments fluid may enter the space along at least one edge of the space e.g. a bottom edge thereof, and preferably along at least a bottom and side edges of the space. Fluid may be able to enter the space continuously along each such edge of the space, or through one or more discrete openings provided along the edge.

The transmission cell may be open along one or more edges thereof. In some preferred embodiments, the transmission cell is open along a bottom edge and/or at least one side edge thereof i.e., along the entire edge. The transmission cell may be open along a bottom and both side edges thereof. This may enable fluid to enter the space through the relevant edges thereof. In other embodiments, one or more discrete openings may be provided along the one or more of the edges of the transmission cell.

Preferably the fluid may enter the space between the first and second walls e.g. windows at one or more points around the edges of the first and second walls. This may be achieved by discontinuously joining the walls to one another around the periphery thereof, or by leaving the walls unattached around the entire periphery thereof. In preferred embodiments the first and second walls are unattached to one another along at least one of the sets of opposed edges thereof to provide an opening or openings through which fluid may enter the space. For example, the walls may be unattached along the opposed bottom and side edges of the walls. The walls may additionally be unattached along the top edges thereof. Having the walls unattached to one another along at least some edges thereof also enables the movable window(s) to be more easily moved into and out of the transmission cell in the applicable direction or directions. In other embodiments, there may be some joining of at least some of the edges of the walls, provided that there are openings to permit the passage of fluid into the interior space defined between the joined areas.

It will be appreciated that the transmission cell does not provide a sealed chamber in which fluid is retained during testing of a sample, but rather enables the flow of fluid into and out of the space between the first and second walls. This allows movement of a movable window to drive fluid out of the transmission cell, or draw fluid into the transmission cell, to enable fluid samples to be renewed, and promote cleaning of the windows. The apparatus may enable a more representative sample of a fluid to be taken.

Preferably the apparatus is configured such that fluid enters the space between the first and second walls when the transmission cell is immersed in fluid. The transmission cell is preferably located at a distal end of the apparatus. The fluid may then enter the transmission cell when the distal end of the apparatus is dipped in fluid. In some embodiments, the apparatus may be used for online testing. The apparatus may then be configured such that fluid enters the space between the first and second walls when at least the transmission cell of the apparatus is mounted so as to be immersed in a volume of fluid.

In accordance with the invention in any of its aspects or embodiments, the apparatus comprises a first movable window which is movable relative to the first and second fixed walls to move the at least a portion of the window into and out of the test region. The apparatus is operable to cause the window to move in this manner. It will be appreciated that the apparatus may be operable to cause the window to move in any of the manners discussed herein. The at least a portion of the first movable window (or any further movable window) that may be moved into and out of the test region is preferably only a portion of the respective window. In other words, only a portion of the window is disposed in the test region. In some embodiments the window may then be movable to dispose another portion thereof in the test region, which, as discussed below, is preferably a portion of different thickness to the (first) portion.

The first movable window is preferably movable so as to move the at least a portion of the movable window repeatedly into and out of the test region. The movable window may be mounted in any suitable manner relative to the first and second walls to permit such movement. In preferred embodiments the first movable window is mounted to a window carrier that is movable relative to the first and second fixed walls. The window carrier is then movable to provide the required movement of the first movable window. The first movable window may be fixedly mounted to the window carrier. The apparatus is operable to cause movement of the window carrier and hence the movable window.

The movement of the first movable window to bring the at least a portion of the window into or out of the test region involves movement of the window to move the at least a portion thereof within the transmission cell. The movement into or out of the test region is a movement that is carried out before or after performing a measurement with the at least a portion of the window in the test region respectively. The movement into or out of the test region (and preferably both) may involve movement of the at least a portion of the window within the space between the first and second fixed walls e.g. windows in which a fluid sample is received. The movement may be a movement in which the at least a portion of the window remains in contact with a fluid to be tested. The first movable window may move in order to move the at least a portion thereof into or out of the test region in a manner such that a differing amount of the first movable window is located within the transmission cell, or the entire window may remain located in the transmission cell before and after movement of the window to move the at least a portion thereof into or out of the test region. Any movement of the first movable window relative to the first and second fixed walls will prompt some exchange of fluid in use, providing some cleaning effect, and renewal of the sample to be tested. The movement need not be to such an extent that the first movable window or the at least a portion thereof, enters or leaves the space between the first and second walls from or to a position outside the space, or enters or leaves the transmission cell or fluid completely. It is preferable that the first movable window does not move to or from a position entirely outside the transmission cell, at least between measurements, enabling a more compact and simple apparatus to be provided. This may avoid the need to provide guiding means for guiding movement of the window or at least a portion thereof into and out of the transmission cell. Thus, in preferred embodiments, the movement of the first movable window to move the at least a portion thereof into or out of the test region is a movement to an extent to move the at least a portion thereof into our out of alignment with the test region. The movement of the first movable window to move the at least a portion thereof into the test region is preferably a movement in which at least a portion of the movable window, which preferably comprises the at least a portion thereof to be moved into the test region, and optionally the entire window, remains within the transmission cell or within the space between the first and second fixed walls. The movement may be a movement in which at least a portion of the movable window, which preferably comprises the at least a portion thereof, and optionally the entire window, remains in contact with fluid in the transmission cell. The movement the first movable window to move the at least a portion thereof out of the test region is preferably a movement in which at least a portion of the movable window, which preferably comprises the at least a portion thereof to be moved out of the test region, and optionally the entire window, remains within the transmission cell or within the space between the first and second fixed walls. The movement may be a movement in which at least a portion of the movable window, which preferably comprises the at least a portion thereof, and optionally the entire window, remains in contact with fluid in the transmission cell. Nonetheless, the first movable window may be movable to a greater extent, at least under some circumstances. For example, movement of the first movable window between measurements may be a movement in which at least a portion of the window, and optionally the entire window remains within the transmission cell, with the first movable window being movable relative to the first and second fixed walls to a greater extent to a maintenance position, at least for periodic overhaul, or more extensive cleaning. For example, the first movable window may be movable to a maintenance position in which the first movable window is entirely disposed outside the transmission cell i.e. outside the space between the first and second fixed walls. The window will then be located out of contact with fluid.

In alternative embodiments, the movement of the first movable window to bring the at least a portion of the window into the test region i.e. for measurement may move the window into the space between the first and second fixed walls from a position outside the space. The movable window may be moved from a location outside the transmission cell into the transmission cell. The movable window may be moved into contact with a fluid to be tested i.e. from a position in which it does not contact the fluid. Conversely the movement of the first movable window to move the at least a portion thereof out of the test region i.e. after measurement may move the first movable window to a position out of the space defined between the first and second fixed walls e.g. out of the transmission cell. The first movable window may be movable into a position in which it is located out of a fluid to be tested.

The window as a whole may be moved in any of the above manners e.g. into or within the space between the first and second fixed walls, or into or within the transmission cell etc. rather than merely at least a portion thereof.

The first movable window may be movable between a position in which the at least a portion thereof is located in the test region and a position in which no part of the window (or preferably any window carrier) is located in the test region. This may enable fluid to more easily enter the test region.

The first movable window may be movable linearly or rotationally to bring the at least a portion thereof into the test region. Similarly, movement of the first movable window to move the at least a portion thereof out of the test region may involve linear or rotational movement. Movement of the window to move the at least a portion thereof into and out of the test region may comprise a combination of linear and rotational movement, although preferably movement both into and out of the test region uses either linear or rotational movement. The first movable window may be slidable to move the at least a portion thereof into and out of the test region. In general, the first movable window may be linearly movable or rotatably movable.

Movement of the first movable window may be achieved using appropriate movement of a window carrier. The window carrier may therefore be rotationally or linearly movable. In some embodiments the window carrier is a slidable window carrier. In other embodiments the window carrier may be a rotatable carrier. However, a window carrier need not necessarily be used. For example, the first moveable window may be rotationally mounted so as to rotate about an axis for moving the at least a portion thereof into and out of the test region.

Movement of the first movable window to move the at least a portion thereof into and/or out of the test region is a predefined movement. This movement may be predefined by the operation of a mechanism that drives the movement, as discussed below. The movement is preferably along a predetermined path. The movement of the first movable window to move the at least a portion thereof out of the test region may be along the same or a different path to its movement to move the at least a portion thereof into the test region. In embodiments, the movement of the first movable window to move the at least a portion thereof out of the test region is in the same or an opposite direction to the movement of the first movable window to move the at least a portion thereof into the test region. For example, where the first movable window is rotatably movable relative to the first and second fixed walls along a first rotational direction to move the at least a portion thereof into the test region, movement of the first movable window to move the at least a portion thereof out of the test region may be along the same direction to provide a continuation of the path traveled into the test region, or the window may be moved along the same path but in the opposite direction traveled to move the at least a portion thereof into the test region. It will be appreciated that more complex arrangements may be used, in which movement of the first movable window to move the at least a portion thereof into or out of the test region is not merely along the same or opposed directions, and combinations of different types of movement e.g. linear or rotational may be used. Preferably the movement of the first movable window to move the at least a portion thereof into and out of the test region is in opposed directions along the same path. This may provide a more space efficient arrangement.

The position of the first movable window relative to the first and second fixed walls when the at least a portion thereof is in the test region may be referred to as a test position.

The first movable window may be movable relative to the first and second fixed walls between a non-test position and a test position relative to the first and second fixed walls in which the at least a portion thereof is disposed in the test region. The non-test position is preferably a position in which no portion of the first movable window is located in the test region. This may facilitate fluid entry into the test region. The method may comprise operating the apparatus to move the first movable window from such a non-test position into the test position, and subsequently from the test position to the non-test position. In these embodiments the first movable window moves into the test position from the non-test position and returns to the same non-test position after testing. The first movable window may return to the non-test position after completion of a measurement cycle. Movement of the first movable window between the non-test position and the test position, or from the test position to the non-test position may be direct or, in embodiments in which the first movable window includes portions of differing thickness, or a second movable window is provided, via a further position in which a further portion of the first movable window is located in the test region, or at least a portion of a second movable window is located in the test region. The test position is a position in which a measurement is taken. The non-test position is a position where no measurement is taken i.e. that is used between taking measurements. The non-test position may correspond to the "third" position mentioned below. The non-test position may provide a storage position of the window.

In some preferred embodiments the first movable window is arranged to move linearly between the non-test position and the test position. The first movable window may be arranged to reciprocate between the non-test position and test position. The non-test position may be a retracted position. In other embodiments the first movable window may move rotationally between the non-test and test positions. The non-test position may be a position in which the window is outside the transmission cell. The non-test position may be a position in which the window is located outside the space defined between the first and second fixed walls. The non-test position may be a position in which the window does not contact a fluid in the transmission cell. The non-test position may be located above or to one side of the space between the first and second fixed walls. However, preferably the non-test position is a position in which at least a portion of the first movable window e.g. comprising the at least a portion thereof, or the entire first movable window is within the transmission cell. The non-test position is preferably a position in which at least a portion of the first movable window e.g. comprising the at least a portion thereof or the entire window is within the space defined between the first and second fixed walls. The non-test position may be a position in which at least a portion of the first movable window e.g. comprising the at least a portion thereof or the entire window is in contact with a fluid in the transmission cell.

The first movable window may be movable so that the at least a portion thereof moves into or out of the test region from above or from one side. The first movable window may be movable into a test position in which the at least a portion thereof is in the test region from a first e.g. non-test position located above or to one side. As mentioned above, it is envisaged that the first movable window may enter the space between the first and second fixed walls to cause the at least a portion thereof to move into the test position, although this is not necessarily the case, and the window may enter the space to a greater extent, or move entirely within the space (although the window may alternatively move in an opposite manner so as to enter the space to a lesser extent). Where the first movable window is movable into a test position in which the at least a portion thereof is located in the test region from a first e.g. non-test position above the test position, it will be appreciated that while the window may be linearly movable from the non-test position into the test position, it may alternatively be rotationally movable from the non-test position to enter the test position from one side. The first movable window may similarly move in order to move the at least a portion thereof out of the test region i.e. out of a test position to a position above or to one side thereof. The first movable window may enter the test position from one side and leave from the same or an opposite side thereof.

The apparatus is operable to cause the at least a portion of the first movable window to move into and out of the test region. The apparatus is operable to cause the at least a portion of the first movable window to selectively move into and out of the test region in this way. The apparatus may comprise any suitable means which is operable to cause the first movable window to move so as to move the at least a portion thereof into and out of the test region i.e. to move the window into and out of a test position. The movement of the first movable window may be from or to a non-test position. The means may comprise a single means for movement into the test region and movement out of the test region, or different means for movement into and out of the test region. The means may also be arranged to cause movement of the first movable window in any of the other manners described herein. The means may comprise a mechanical mechanism, or an electrical e.g. electronic arrangement, or a combination thereof.

The apparatus may be operable in response to one or more actions by a user to cause the first movable window to move with respect to the first and second fixed walls to move the at least a portion thereof into or out of the test region, or to cause any other movement of the first movable window described herein. Thus, such movement of the window may be at least initiated by a user action or actions. In some preferred embodiments the apparatus is manually operable by the user. For example, the apparatus may comprise one or more operator controls, such as one or more button, slider, grip, level, dial, or a combination thereof etc. It will be appreciated that the movement of the first movable window may then be accomplished using a mechanical or electrical e.g. electronic means, or a combination thereof. For example, a piezoelectric arrangement may be used. The action of a user may directly or indirectly cause the movement of the first movable window. In some embodiments the movement of the first movable window is manually driven by a user. The user may actuate a mechanical mechanism for causing movement of the first movable window into or out of the test region. For example, the first movable window may be slid linearly into and out of the test region using a spring loaded pushrod operated manually by a user, or may be swung in from the side on an end of a sprung lever operated by the user squeezing a grip, and so on. In other embodiments movement of the window may be automatically driven once initiated by a user. This may be accomplished mechanically e.g. under the action of a spring. A hydraulic arrangement might be used. In other embodiments the movement of the window may be driven electrically e.g. by an electric motor. This may be the case whether the movement is initiated by a user action or not.

The user may be required to perform the same or a different operation e.g. manual operation to move the first movable window to move the at least a portion thereof into and out of the test region e.g. to press the same or a different button, rotate a dial, apply and then release a grip or lever, and so on. It is envisaged that the window may be arranged to automatically move so as to move the at least a portion thereof out of the test region after measurement is complete, e.g. after a given time, or after a measurement has been taken. However, preferably one or more actions are required by the user to cause the first movable window to move in order to cause the at least a portion thereof to move both into and out of the test region.

In other embodiments, the apparatus may be automatically operable e.g. under the control of a set of one or more processors to cause the first movable window to move so as to move the at least a portion thereof into or out of the test region, or in any other manner. In these embodiments the movement of the first movable window may be electrically e.g. electronically initiated and driven e.g. using an electric motor. The movement may be achieved using a mechanical mechanism that is controlled electronically, or solely through electronic means. Movement of the first movable window into the test region may be automatically initiated e.g. at a predetermined time or interval, or at the start of an electronically controlled measurement cycle. Such a cycle may be initiated in response to a received control signal. Electrically e.g. electronically actuated arrangements may be particularly appropriate where the apparatus is used for online testing of samples.

Thus, in accordance with the invention, movement of the first movable window may be initiated automatically or in response to one or more actions by a user. Movement of the first movable window (once initiated) may be driven automatically (whether mechanically or electrically), or may be driven manually by a user. In general, movement of the first movable window may occur under the control of an actuator arrangement, which may be e.g. a mechanical or electrical actuator arrangement or a combination thereof. Hydraulic arrangements may also be envisaged. Whatever form of actuation is used, movement of the first movable window may be remotely actuated.

The sample testing apparatus may include only a single window i.e. the first movable window that is movable relative to the first and second walls, or may comprise first and second movable windows. When at least a portion of a movable window is located in the test region, the optical path traveled by electromagnetic radiation between the fixed walls includes only one thickness of window substrate i.e. provided by the at least a portion of the movable window e.g. of the applicable portion of the first or second movable window. The or each window may include a single thickness of window substrate. Each window is preferably a single ply window. Only one movable window is disposed between the first and second fixed walls in the given test region in the path of radiation at any time for performing a test.

In some embodiments, regardless of whether any additional movable window is provided, the first movable window is of constant thickness. In these embodiments, the exact position of the window relative to the first and second fixed walls to position at least a portion thereof in the test region may not be critical, provided that at least a portion of the first movable window lies in the path of radiation introduced into the cell and traveled before detection. Wherever the radiation is incident upon the first movable window when disposed between the first and second fixed walls, the same gap will be provided on one or both sides thereof, and hence the same path length through the sample will be provided. Where the first movable window is of constant thickness, in some simple embodiments a single movable window may be provided. However, as discussed below, preferably a second movable window of different thickness and movable relative to the first and second fixed walls is then provided to enable measurements based upon different path lengths through the sample to be obtained.

In other embodiments the first movable window is of non-uniform thickness. The at least a portion of the first movable window may be at least a portion of a first portion thereof, the first movable window further comprising a second portion of different thickness to the first portion. The window therefore may comprise first and second portions of differing thickness. The second portion may be thicker than the first portion. The apparatus may further be operable to cause the first movable window to move with respect to the first and second fixed walls to move at least a portion of the second portion of the window into and out of the or a test region of the transmission cell. The at least a portion of the second portion of the window may be moved into the or a test region (for performing a measurement) before or after movement of the at least a portion of the first portion of the window into the test region (for performing a measurement), or, where different test regions are used, it may be envisaged that at least a portion of both first and second portions might simultaneously be locatable in test regions. The direction of the variation in thickness of the window may be in a direction of movement of the window. Preferably the variation in thickness of the movable window is in a height direction of the movable window. The first and second portions may be located one above the other. Such embodiments are particularly suitable where the window is arranged to move linearly relative to the first and second walls. However, depending upon the direction in which the movable window is intended to move the at least a portion of the relevant portion thereof into the or a test region, it is envisaged that the first and second portions may be located side by side or otherwise. In some preferred embodiments, regardless of the way in which the window moves, the first and second portions may be located at first and second ends of the window.

It will be appreciated that portions of different thickness e.g. a first and second portion of the first movable window may be portions of an integral window. Alternatively, the portions of the window may be provided by separate window pieces of different thickness attached to one another. The first movable window (or any further movable window) may thus comprise a single window piece, or multiple window pieces attached to one another. The first and second window portions may be contiguous or separated by another window portion. Each portion of the window i.e. the first and second portions, and any further portion, are window portions.

The first movable window may continuously vary in thickness e.g. being wedge shaped. The wedge angle of the window may be selected as desired. More preferably the window may have a stepped variation in thickness. The window may comprise a first portion of a first thickness and a second portion of a different second thickness, with a stepped discontinuity between the portions of different thickness. The window may then include only first and second portions of differing thickness, separated by a single stepped discontinuity. In these embodiments in which the first movable window includes portions of different thickness, it is important that radiation passes through the appropriate portion of the window during a measurement, to ensure that it experiences the intended path length. At least a portion of the relevant portion of the window should be located in a test region for performing a measurement (preferably being the same test region for the first and second portions). The thickness of the at least a portion of the window should be constant over the extent of the test region to ensure that a predefined path length is provided for radiation incident on the portion of the window. Where the window varies continuously in thickness, it will be appreciated that the exact positioning of the window relative to the fixed walls is even more important. It may be necessary to align a particular portion e.g. line across the window with the test region. Such embodiments may necessitate a more limited test region e.g. defined by a narrow beam of radiation. Where a window exhibits portions of differing thickness, a stepped discontinuity is preferable to a continual variation in thickness for these reasons.

In embodiments in which the first movable window comprises first and second portions of differing thickness, the apparatus may be operable to cause the first movable window to move relative to the first and second fixed walls such that at least a portion of the first portion and at least a portion of the second portion of the window may be selectively located in the (same) test region i.e. such that either the at least a portion of the first or the at least a portion of the second portion is located in the test region at a given time. Thus, the at least a portion of the first movable window is preferably at least a portion of the first portion thereof, the apparatus being operable to cause the first movable window to move with respect to the first and second fixed walls to move the at least a portion of the first portion of the window into and out of the test region, and the apparatus is further operable to cause the first movable window to move with respect to the first and second fixed walls to move the at least a portion of the second portion of the window into and out of the test region. Preferably the at least a portion of the first portion and the at least a portion of the second portion may be sequentially located in the test region. The sequence may be in either order. Measurements may then be taken with the at least a portion of the first portion and the at least a portion of the second portions respectively in the test region. The apparatus may be operable to perform a cycle in which the first movable window is moved to locate the at least a portion of the first portion and the at least a portion of the second portion of the window sequentially in the test region for performing respective measurements.

It will be appreciated that the first movable window might similarly be movable to locate at least a portion of a first portion and at least a portion of a second portion of the window in the test region even where such first and second portions are of the same thickness, in order to promote fluid movement for cleaning and sample renewal between measurements. Measurements may then be taken with the at least a portion of the first and second portions respectively in the test position. The first and second portions might be provided at respective opposite ends of the window. Such an arrangement might be envisaged with a rotatably mounted window.

In general, the first movable window may be movable between at least a first position relative to the fixed walls in which at least a portion of the first portion thereof is located in the test region and a second position in which at least a portion of the second portion thereof is located in the test region. The window is preferably movable between the first and second positions and a third position in which no portion of either the first or second portions is located in the test region, and preferably in which no portion of the window is located in the test region. This may facilitate fluid entry into the test region.

Where the first movable window is of varying thickness, the apparatus provides the opportunity to pass electromagnetic radiation through different portions of the window so as to result in the radiation experiencing different path lengths through the sample fluid. This may enable two different measurements to be obtained based on the same test fluid and using different path lengths. Accordingly, when the at least a portion of the first portion of the movable window is located in the or a test region, an optical path of a first length is defined through the sample in the test region between the first and second fixed walls for electromagnetic radiation introduced through the window of the first wall, and when the at least a portion of the second portion of the movable window is located in the or a test region, an optical path of a second length is defined through the sample between the first and second fixed walls in the test region for electromagnetic radiation introduced through the window of the first wall, the first and second path lengths being different. The second path length may be less than the first. Preferably at least a portion of the first portion and at least a portion of the second portion of the window may be selectively located in the same test region. Preferably either the at least a portion of the first portion or the at least a portion of the second portion may be located in the test region at any given time. The at least a portion of the first portion and the at least a portion of the second portion of the window may be selectively moved into and out of the (same) test region. Preferably the apparatus is arranged such that movement of the first movable window to locate the at least a portion of one of the first and second portions in the test region e.g. of the second portion results in movement of the at least a portion of the other portion out of the test region.

Alternatively, the ability to obtain two different measurements based on the same test fluid but using different path lengths may be provided by using a second movable window having at least a portion of different thickness to the at least a portion of the first movable window. Preferably the apparatus comprises such a second movable window. The second, movable window is movable with respect to the first and second fixed walls to locate the at least a portion thereof in the or a test region of the apparatus (for performing a measurement). The second movable window may be moved to move the at least a portion thereof into the or a test region (for performing a measurement) before or after movement of the first movable window to move the at least a portion thereof into the test region (for performing a measurement), or, where different test regions are used, it may be envisaged that both the at least a portion of the first and second movable windows might simultaneously be locatable in test regions.

Preferably the apparatus is operable to selectively move the first movable window to locate the at least a portion of the first movable window in the test region, and to move the second movable window to locate the at least a portion of the second movable window into the (same) test region, and is preferably operable to move the first and second movable windows to locate the at least a portion of the first movable window and the at least a portion of the second movable window sequentially in the (same) test region. The at least a portion of each window may be located in the test region in any order. It will be appreciated that either the at least a portion of the first movable window, or the at least a portion of the second moveable window is located in the test region at any time. The apparatus may be operable to perform a cycle in which the first and second movable windows are moved to locate the at least a portion of each of the first and second movable windows in the test region for performing respective measurements.

The second movable window, is, like the first movable window, movable relative to the first and second fixed walls. The first and second movable windows preferably are not movable relative to one another. The apparatus is operable to selectively move the at least a portion of the first and the at least a portion of the second movable windows into and out of the (or a) test region. Thus, in some embodiments, the apparatus further comprises a second movable window, the movable window being movable with respect to the first and second fixed walls, wherein at least a portion of the second movable window is of different thickness to the at least a portion of the first movable window. The apparatus is operable to cause at the least a portion of the first and the at least a portion of the second movable windows to be selectively located in the (or a) test region. In preferred embodiments the first and second movable windows may be mounted to the same movable window carrier. This may ensure that movement of one window results in movement of the other window. Preferably the apparatus is arranged such that movement of one of the first and second movable windows to locate the at least a portion thereof in the test region results in movement of the other of the first and second movable windows to move the at least a portion thereof out of the test region. In preferred embodiments, the second movable window is of different thickness to the first movable window, and the apparatus is operable to move the first and second movable windows to selectively move the at least a portion of the first movable window and at least a portion of the second movable window into the test region. In any of the embodiments in which first and second movable windows are provided, the first and second movable windows are preferably of the same material. The first and second movable windows are preferably each of constant thickness (although of different thickness to each other).

When the at least a portion of the first movable window is located in the test region, an optical path of a first length is defined through the sample between the first and second fixed walls in the test region for electromagnetic radiation introduced through the window of the first wall, and when the at least a portion of the second movable window is located in the, or in some embodiments a, test region, an optical path of a second length is defined through the sample between the first and second fixed walls in the test region for electromagnetic radiation introduced through the window of the first wall, the first and second path lengths being different. The second path length may be less than the first. Measurements may be taken with the at least a portion of the first and the at least a portion of the second movable windows located respectively in the (applicable) test region.

As described earlier, when the at least a portion of the first movable window is located in the or a test region, a gap is defined between the at least a portion of the first movable window and one or both of the first and second fixed walls in the test region of the cell. Where the first movable window varies in thickness, and the at least a portion of the first movable window is at least a portion of the first portion thereof, the second portion of the window may be thinner or thicker than the first portion. In embodiments the second portion is preferably thicker than the first portion. Likewise, a second movable window (or the at least a portion thereof) may be thicker or thinner than a first movable window (or the at least a portion thereof), where provided, and is preferably thicker. When the at least a portion of the second portion of the first movable window or at least a portion of the second movable window is located in the or a test region, a gap may or may not be defined between the at least a portion of the second portion of the first movable window or the at least a portion of the second movable window and one or both of the first and second fixed walls at least in the test region of the cell. For example, the at least a portion of the second portion or at least a portion of the second movable window could be of a thickness such that it contacts the wall on one or both sides thereof. Where contact is on both sides, this may then define a zero path length through the sample. However, preferably a gap is defined on both sides of the at least a portion of the second portion of the first movable window, or the at least a portion of the second movable window at least in the or a test region i.e. between the at least a portion and the first and second fixed walls respectively. Thus, first and second gaps are preferably defined on each side of the at least a portion of the second portion of the first movable window, or the at least a portion of the second movable window.

The ability to obtain two different measurements on the same test fluid based on two different path lengths through the sample is advantageous for a number of reasons. Firstly, this may provide an inbuilt reference. The length of the measurement path may be well compensated for temperature variation. For example, where different portions of a first movable window are used to provide both measurements, these will be of the same material. A second movable window may be constructed of the same or similar material to the first movable window. The thickness variation within the first movable window, or between first and second movable windows may be arranged to be relatively small. A further key advantage of being able to perform two different measurements is that this enables the dependency of concentration upon the intensity of the source to be removed. The infra-red absorption may thus be determined as the difference between the signal measured at the first and second test positions, i.e.:

$$\log(I_{thick}) - \log(I_{thin}) = [\log(I_O) - \alpha \cdot c \cdot L_{thick}] - [\log(I_O) - \alpha \cdot c \cdot L_{thin}] = \alpha \cdot c \cdot (L_{thin} - L_{thick})$$

where $I_{thick}$ is the power of the radiation detected after passing through the thicker window or window portion, and $I_{thin}$ is the power of the radiation detected after passing through the thinner window or window portion, where the radiation travels along a path length $L_{thick}$ through the sample when incident on the thicker window or window portion, and travels along a path length $L_{thin}$ through the sample when incident on the thinner window or window portion, c is the concentration of the absorbing substance, and $\alpha$ is an absorption coefficient.

Being able to remove the dependence upon the intensity of the radiation incident upon the cell is beneficial to measurement accuracy, and also enables quick measurements to be more easily made with a portable apparatus. This is because radiation sources at an appropriate wavelength for testing fluids, e.g. infrared sources, are typically thermal devices, for which emitted power is strongly dependent on temperature (of the order of the 4th power of absolute temperature). Such devices take time to warm up and reach a stable temperature. By avoiding the need for the source to do this, battery power of a portable apparatus may be conserved, as the apparatus need not be turned on for extended periods required for the source to reach a stable temperature before a measurement is taken, and delay between performing measurements may be reduced.

The first and second movable windows are discrete windows. For example, such windows may be discrete windows in a window carrier, which may be separated from one another by the carrier substrate. In other embodiments, it is envisaged that first and second movable windows might be mounted relative to one another at different rotational positions. The windows may then be arranged to rotate about a common axis of rotation. The windows may or may not be associated with a window carrier in such embodiments.

Where the apparatus comprises first and second movable windows, the windows may be spaced from one another. The windows may be mounted to a common window carrier. The windows are then not independently movable. The window carrier may be, for example, slidably or rotatably movable. The windows may be spaced from one another by the window carrier. The windows may be spaced from one another along a length of a linear window carrier. In some embodiments the windows are mounted to the window carrier side-by-side, or one above the other. This may be appropriate where the window carrier is arranged to move linearly. In other embodiments, the windows may be mounted to a rotatable window carrier at different rotational positions. For example, the windows may be mounted to different arms of such carrier, or to different locations around the circumference of a rotating window carrier e.g. in the form of a disk.

Preferably the first and second movable windows are each of uniform thickness. Thus the entirety of the first movable window may be of different thickness to the entirety of the second movable window.

More complex arrangements might be envisaged to enable measurements to be taken based on more than two different path lengths through the test fluid e.g. using one or more further movable window having at least a portion of a different thickness to the first and second movable windows, wherein the at least a portion of the or each further movable window may be located in the test region, or, using a first movable window having more than two portions of differing thickness, at least a portion of each of which portions may be selectively located in the test region. Preferably where multiple movable windows are provided, each is of constant thickness. Similarly, it is envisaged that where multiple windows are provided, at least some may include portions of different thickness. However, the provision of a first movable window with regions of only two different thicknesses, or the use of only two movable windows is preferable in providing a more compact apparatus, and still providing the advantages discussed above through being able to make multiple measurements on a particular test fluid. Preferably where the first movable window is of non-uniform thickness, it includes only two portions of differing thickness, and, where multiple movable windows are provided, only two such windows are provided. Each such window is preferably of uniform thickness.

In preferred embodiments in which the first movable window includes portions of different thickness, or the apparatus comprises first and second movable windows having at least portions of different thickness, at least a portion of each of the different portions of the first movable window, or at least a portion of each of the first and second movable windows as appropriate, are preferably selectively locatable in the same test region of the apparatus i.e. "the" test region. The apparatus preferably defines a single test region. This means that movement of the first movable window (where the first movable window includes portions of different thickness), or movement of the first and second movable window where a second movable window is provided, is required in order to move the at least a portion of the first portion of the first movable window out of the test region and the at least a portion of the second portion thereof into the test region or vice versa, or, in the other embodiments, to move the at least a portion of the first movable window out of the test region and the at least a portion of the second movable window into the test region or vice versa. This is advantageous, as the movement of the movable window or windows relative to the fixed walls of the cell helps to clean the surfaces of the cell and windows as described above, and also helps to renew the sample in the cell. Furthermore, only a single set of a source and detector need be provided, allowing a more compact apparatus to be provided. This is advantageous particularly in providing a portable hand held unit including the apparatus. However, more complex arrangements can be envisaged in which multiple test regions might be provided e.g. for use with different portions of a first movable window of variable thickness e.g. one above the other or side by side, or for use with different movable windows. This may be achieved by providing multiple distinct regions at which electromagnetic radiation e.g. an electromagnetic radiation beam, may enter the transmission cell e.g. through different portions of the window associated with the first fixed wall, and be detected. Each test region may then be defined in the manner described in relation to "the" test region herein, and may include any of the features described in relation to "the" test region. The detector and/or source associated with any further test region may be in accordance with any of the embodiments described herein in relation to "the test region". In these embodiments, movement of at least a portion of a first portion of the first movable window into the (first) test region may locate at least a portion of a second portion of the window in its own different test region (i.e. a second test region), or at least a portion of a first and at least a portion of a second movable window might be simultaneously be locatable in respective test regions. In such further embodiments, any of the features regarding the test region, or the movement of the windows or portions thereof into the test region may be applicable to the relevant test region for a given window, or portion thereof, to the extent they are not mutually exclusive.

Whether or not the first movable window is of varying thickness, or whether a second movable window is provided, the step of moving the at least a portion of a movable window (whether the first movable window or a second or further movable window) into or out of the test region involves a predefined movement of the window. The step of moving the at least a portion of a movable window into the test region may comprise moving the movable window to a preset position relative to the first and second fixed walls. The preset position may be a position in which a reference position on the movable window is in alignment with a reference position on the first and/or second fixed walls. For example, a particular line across the movable window may be aligned with a particular line between the first and second fixed walls along which electromagnetic radiation will pass prior to detection. Where the first (or any further) movable window includes portions of different thickness, the window may be movable to a first preset position relative to the first and second fixed walls, in which at least a portion of the first portion thereof is located in the test region, and to a second preset position relative to the first and second fixed walls in which at least a portion of the second portion thereof is located in the test region. Movement of a window into a preset position may be achieved by limiting the travel of the window relative to the first and second fixed walls. This may be carried out in various ways.

In some embodiments the apparatus may comprise locating means for locating the movable window relative to the first and second fixed walls such that the at least a portion thereof is in the test region. The locating means may be arranged to temporarily retain the movable window in a preset position relative to the first and second fixed walls. The locating means may comprise e.g. a stop for limiting the travel of the movable window relative to the first and second fixed walls. Where a movable window i.e. the first movable window includes portions of different thickness, locating means may be provided for locating the movable window relative to the first and second fixed walls in a first preset position such that at least a portion of the first portion thereof is in the test region and for locating the movable window relative to the first and second fixed walls in a second preset position such that at least a portion of the second portion thereof is in the test region. The locating means may comprise first and second locating means for locating the window with the at least a portion of the first and the at least a portion of the second portions thereof in the test region respectively. While a preset position may be determined by a mechanical arrangement, in other embodiments, movement of a movable window may be controlled electronically. In these embodiments moving the movable window to a preset position relative to the first and second fixed walls may be achieved by driving the window through a preset distance relative to the first and second walls. Thus, the or each preset position may correspond to a given amount of travel of the movable window relative to the first and second fixed walls. Of course, where multiple test regions are provided, the step of moving the at least a portion of a movable window into a test region may involve moving the window to a preset position in any of the above manners. Locating means may be provided for locating a movable window relative to the first and second fixed walls such that the at least a portion thereof is in the applicable test region.

The need to accurately locate a portion of a movable window relative to the first and second fixed walls so as to locate the portion in the test region is greater where a single movable window includes regions of differing thickness, in particular where a continuous variation in thickness is used. Such embodiments may advantageously use an electronic driving arrangement to move the window through preset distances relative to the first and second fixed walls to ensure that the at least a portion of the first and the at least a portion of the second portion of the window are appropriately aligned with the first and second fixed walls in the test region. Where a movable window is of uniform thickness, the need for the window to be in a preset position relative to the first and second fixed walls is less important. Simply moving the window into the transmission cell may be sufficient to locate at least a portion of the window in the test region. Electronically actuated arrangements also provide the ability to drive the window more rapidly, helping to enhance the cleaning effect.

Where the first movable window comprises first and second portions of differing thickness, or where first and second movable windows are provided, the apparatus may be operable to sequentially move the at least a portion of the first portion and the at least a portion of the second portion of the first movable window in either order, or the at least a portion of the first and second movable windows in either order, into the test region for performing a measurement. Preferably the at least a portion of the first portion is located in the test region before the at least a portion of the second portion, or the at least a portion of the first movable window is located in the test region before the at least a portion of the second movable window. Preferably this is achieved through movement of a window carrier. The window carrier may comprise one or more components. In preferred embodiments in which first and second movable windows are provided, the windows are mounted to the same window carrier. Movement of the first movable window to locate the at least a portion of the other of the first or second portion thereof, or of the other of the first or second movable window to move the at least a portion thereof into the or a test region (preferably the same test region), may be achieved by further movement of the window carrier relative to the first and second fixed walls after movement of the window carrier to locate the at least a portion of the first or second portion of the first movable window, or the at least a portion of the first or second movable window, in the or a test region (preferably the same test region). The further movement may be a continuation of the movement of the window carrier in the same direction. Where provided, the first and second movable windows are preferably mounted such that the windows may not move relative to one another. In this way, movement of the window carrier to move one window into the test region will result in movement of the other window e.g. to move it out of the test region. Of course, other more complex embodiments may be envisaged in which different windows are associated with independently movable window carriers etc. A window carrier may similarly be used where multiple test regions are used, for moving portions of a first movable window, or first and second movable windows, into an applicable test region, either sequentially, or, in some embodiments, simultaneously.

In other embodiments, rather than using a window carrier, the first, or where provided, first and second movable windows, may be rotationally mounted to define a rotor that is rotatable to move the at least a portion of the or each window portion or window into and out of the test region e.g. sequentially. First and second movable windows may define arms of such a rotor.

Any of the techniques described above for moving the first movable window to locate at least a portion thereof in the test region, or to move the at least a portion thereof out of the test region, may be used for moving the window to locate at least a portion of another portion thereof in the test region, or to move the at least a portion of a second movable window into or out of a test region. Operation of the apparatus to move the at least a portion of the other portion of the first movable window, or the at least a portion of the other one of the first and second movable windows, into the test region may be initiated in response to one or more actions of a user i.e. manually, or may be initiated automatically e.g. using an electronic system. The movement of the window or windows may then be driven manually or automatically e.g. electrically or mechanically. For example, the user may initiate the movement after a first measurement has been taken based on one of the windows or window portions. In other embodiments, the apparatus may be arranged to perform an automatic cycle in which at least a portion of a first portion and at least a portion of a second portion of a first movable window, or at least a portion first movable window and at least a portion of a second movable windows, are sequentially, in either order, moved into the test region. The cycle may be automatically or user initiated. Any of the above techniques may also be used where multiple test regions are involved.

It will be appreciated that the method of the present invention in the further aspects described below may involve operating the apparatus to cause the first and/or second movable window as appropriate, to move in any of the manners described below.

In embodiments in which the first movable window includes first and second portions of different thickness, the apparatus may be operable to perform a cycle including a first stage in which the first movable window is moved to locate at least a portion of one of the first and second portions of the first movable window in the test region for performing a measurement, and a second stage in which the at least a portion of one of the first and second portions of the first movable window is moved out of the test region with at least a portion of the other of the first and second portions of the first movable window being moved into the test region for performing a measurement. The one of the first and second portions may be the first portion, i.e. such that the at least a portion of the first portion is located in the test region before the at least a portion of the second portion. The second stage may include first and second sub-stages for moving the one of the at least a portion of the first portion and the at least a portion of the second portion of the window out of the test region and moving the at least a portion of the other of the first and second portions into the test region. The apparatus may be arranged such that the first moveable window is moved from a non-test position to the position in which the at least a portion of the one of the first and second portions of the first movable window is located in the test region, and the first movable window may be arranged to return to the non-test position after the at least a portion of the other of the first and second portions of the first movable window has been moved into the test region. The positions of the first movable window relative to the first and second fixed walls in which the at least a portion of the first portion and the at least a portion of the second portion thereof are located in the test region may be referred to as respective test positions. The non-test position may be a non-test position as described earlier. The cycle may be manually or automatically initiated. The apparatus may be arranged to automatically transition between the stages (or, where applicable, substages), or may transition between the stages (or, where applicable, substages) in response to a user input. Performing of a measurement with the at least a portion of the first portion or at least a portion of the second portion of the first movable window in the test region may be initiated automatically or in response to user input. An apparatus for performance of online measurements may be arranged to automatically perform a cycle including the above stages, and to initiate measurements and transition between the stages automatically. Of course, in the event that further portions of the window are provided of different thickness, at least a portion of at least some, or each of the further portions may be located in the test region for measurement one after the other in further stages, before, during or after the stages involving the first and second portions.

In yet other embodiments in which the first movable window is arranged to rotate, rather than being mounted to a rotating window carrier, it is envisaged that the window may define a rotor which is rotatable between a first rotational position relative to the fixed walls in which the at least a portion of the first portion of the window is located in the test region and a second rotational position in which the at least a portion of the second portion of the first movable window is located in the test region. The rotor is preferably movable between the first and second positions and a third rotational position in which no portion of the first movable window is located in the test region. This may facilitate fluid entry into the test region. The first and second portions of the first movable window may be located at respective ends thereof.

In general, the first movable window may be movable between at least a first position relative to the fixed walls in which at least a portion of the first portion thereof is located in the test region and a second position in which at least a portion of the second portion thereof is located in the test region. The positions may be referred to as first and second test positions. The window is preferably movable between the first and second positions and a third position in which no portion of the first and second portion is located in the test region, and preferably in which no portion of the window is located in the test region. This may facilitate fluid entry into the test region.

In embodiments in which the first and second movable windows are provided, the apparatus may be operable to perform a cycle including a first stage in which one of the first and second movable windows is moved to locate the at least a portion thereof in the test region for performing a measurement, and a second stage in which the one of the first and second movable windows is moved to move the at least a portion thereof out of the test region with the other of the first and second movable windows being moved to locate the at least a portion thereof in the test region for performing a measurement. The one of the first and second movable windows may be the first movable window i.e. such that the at least a portion of the first movable window is located in the test region before the at least a portion of the second movable window. The second stage may include sub stages in which the one of the first and second movable windows is moved to move the at least a portion thereof out of the test region and the other of the first and second movable windows is moved to move the at least a portion thereof in the test region. The apparatus may be arranged such that either of both of the first or second moveable windows is moved from a respective non-test position to the position in which the at least a portion of the window is located in the test region, and may be arranged to return to the non-test position after measurement with the at least a portion thereof located in the test region. A non-test position for the second movable window may be defined in any of the manners discussed above in relation to the first movable window. Movement to or from the non-test position may be direct, or via a further position in which the at least a portion of the other of the first and second movable windows is located in the test region. A non-test position for the first and second movable windows may correspond to a non-test position of a window carrier to which the first and second movable windows are mounted. The apparatus may be arranged to automatically transition between the stages (or, where applicable sub stages), or may transition between the stages (or sub stages) in response to a user input. In preferred embodiments the windows are not movable relative to one another, and movement of one window results in movement of the other such that there will be movement of the one window during movement of the other. Performing of a measurement with the at least a portion of the first or second movable window in the test region may be triggered automatically or in response to user input. An apparatus for performance of online measurements may be arranged to automatically perform a cycle including the above stages, and to initiate measurements and transition between the stages automatically. Of course, in the event that further portions of the window are provided of different thickness, the further portions may be located in the test region for measurement one after the other in further stages, before, during or after the stages involving the first and second portions.

In some embodiments in which the first and second movable windows are mounted to a common window carrier, the window carrier to which the first and second movable windows are mounted may be movable between at least a first position relative to the fixed walls in which the at least a portion of the first movable window is located in the test region and a second position in which the at least a portion of the second movable window is located in the test region. The first and second positions may be referred to as test positions. The carrier is preferably movable between the first and second positions and a third position in which neither the at least a portion of the first movable window or the at least a portion of the second movable window is located in the test region, and preferably in which no portion of either window is located in the test region. This may facilitate fluid entry into the test region.

In yet other embodiments in which the windows are arranged to rotate, rather than being mounted to a rotating window carrier, it is envisaged that first and second movable windows may define arms of a rotor which is rotatable between a first rotational position relative to the fixed walls in which the at least a portion of the first movable window is located in the test region and a second rotational position in which the at least a portion of the second movable window is located in the test region. The rotor is preferably movable between the first and second positions and a third rotational position in which neither the at least a portion of the first movable window or the at least a portion of the second movable window is located in the test region, and preferably in which no portion of either window is located in the test region. This may facilitate fluid entry into the test region. In some embodiments, the at least a portion of the first movable window is a first end thereof, and the at least a portion of the second movable window is a second end thereof, and the rotor is further movable between the first and second positions, (and optionally the third position), and fourth or fifth rotational positions in which opposite ends of the first and second movable windows to the first ends thereof are located in the test region respectively. The rotor may be arranged to rotate between the positions in a predetermined order to provide a measurement cycle. Movement in a given direction may sequentially move between positions in which the respective first ends and then second ends of the windows are located in the test region.

In some preferred embodiments the apparatus comprises one or more set of one or more wipers for wiping one, or, where appropriate, preferably each of the sample fluid contacting surfaces of the first movable window during relative movement between the movable window and the first fixed and second fixed walls, and/or for wiping the sample contacting surface of the or each window associated with the first and second fixed walls of the apparatus during relative movement between the first movable window and the first and second fixed walls. A wiper need not be arranged to wipe the entirety of the sample contacting surface, provided that at least the portion that is aligned with the test region in use, or which passes through the test region, is wiped. Preferably each wiper is a resilient wiper. Respective sets of one or more wipers may be provided for wiping the surfaces of the first movable window and the window(s) of the fixed walls. Thus one or more set of one or more wipers may be provided for wiping one or more, and preferably each optical surface of the apparatus. A set of one or more wipers for wiping one or both sample fluid contacting surfaces of the first movable window may be arranged to also wipe one or preferably both of the sample fluid contacting surfaces of a second movable window, or a further set of one or more wipers may be provided for this purpose. In preferred embodiments in which the first and second fixed walls are provided by first and second fixed windows, preferably one or more set of one or more wipers is provided for wiping the sample contacting surfaces of each of the first and second fixed windows. The or each wiper may be arranged to engage the applicable sample contacting surface during relative movement of the first movable window and the first and second fixed walls.

The set(s) of one or more wipers may be located in any suitable position to provide such wiping, and the most appropriate position will depend upon the type of relative movement which occurs between the first (or further) movable window and the first and second fixed walls. In preferred embodiments a set of one or more wipers is provided at either or both of; a leading end of the first movable window or of a window carrier for the first movable window; and an end of the or each window associated with a fixed wall of the cell. The end of the or each window associated with a fixed wall of the cell may be an end closest to an entrance or exit to the transmission cell. The exit or entrance to the transmission cell refers to the entrance or exit through which at least a portion of the first movable window extends in some embodiments when the window moves to move the at least a portion thereof into or out of the test region. The entrance and exit may be the same. In some embodiments wipers are provided associated with each side of the leading end of a window carrier for the first movable window, or on each side of a leading end of the first movable window, facing the first and second fixed walls e.g. windows. A set of one or more wipers at the leading end of the window carrier may engage the or each window associated with the first and/or second fixed walls of the cell as the first movable window moves relative to the walls. A set of one or more wipers at the end of the or each window associated with a fixed wall of the cell may engage the or each side of the first movable window as it moves relative to the fixed walls. The same set of wipers may also wipe a further movable window where provided. Of course, other arrangements might be envisaged. For example, where the first (or further movable window) is arranged to rotate, a set of one or more wipers may be associated with a further rotatable arm that rotates with the first movable window. The arm may pass through the transmission cell before or after movement of the first movable window therethrough.

In some embodiments the apparatus may comprise means for limiting the movement of the first movable window relative to the fixed walls of the transmission cell to prevent the window from being fully removed from the transmission cell. The means may cooperate with the window or a window carrier therefor. Means may be provided for limiting the movement of any further movable window relative to the fixed walls of the transmission cell to prevent the window being fully removed from the transmission cell. The means may be the same means as that which limits movement of the first movable window. For example, limiting means may cooperate with a window carrier having both the first and second movable windows mounted thereto. The limiting means may prevent a window from moving to a position in which any part thereof is outside the transmission cell, or may allow the window to move to a position in which at least a portion thereof is outside the transmission cell. A non test position of the window may be defined by a position in which the window is withdrawn from the transmission cell to the greatest extent allowed by the limiting means. However, as discussed above, a wide range of arrangements are possible, and the window may alternatively be arranged to be fully withdrawn from the cell, or to move entirely within the cell. The most appropriate arrangement will also depend e.g. upon the type of movement of the window e.g. whether linear or rotational etc.

In some embodiments, at least some of the wipers of the one or more set of one or more wipers may cooperate with one another to limit movement of the first movable window relative to the fixed walls e.g. windows of the cell. The wipers may be arranged to prevent movement of the first movable window completely out of the transmission cell. The wipers may be arranged to limit movement of the first movable window by limiting movement of a window carrier therefor. Where a further movable window is present, at least some of the wipers may similarly be arranged to cooperate with one another to limit movement of the further movable window. The wipers may be the same or different wipers as those which limit movement of the first movable window. For example, where first and second movable windows are mounted to the same window carrier, the wipers may limit movement of the window carrier and hence the first and second movable windows. However, it is not necessary that the wipers provide this additional function.

It is envisaged that the apparatus may comprise means for causing the first movable window (and, optionally, any further movable window) to oscillate as it is moved. This may be achieved by providing means for oscillating a window carrier to which the window is mounted. The oscillation of the window may help to promote the cleaning effect and may agitate the sample fluid to help mix it and provide a more representative sample in the transmission cell.

The apparatus may form part of a sample testing unit, which may further comprise a housing. The unit should be configured to enable fluid to enter the transmission cell as described above.

The apparatus may be used in testing an extracted fluid sample.

In some preferred embodiments the apparatus is a portable apparatus, and may be a hand held apparatus. The apparatus may be configured so as to enable the transmission cell to be dipped into a fluid to be tested. The apparatus may further comprise a display and/or one or more user interfaces to enable a user to operate the apparatus. The apparatus may comprise a set of one or more processors. The transmission cell is preferably located at a distal end of the apparatus or unit. The apparatus or unit may be configured as a probe with the transmission cell at a distal end thereof and an operator end at the proximal end. The operator end is intended to be grasped by the user. The apparatus or unit may comprise a connecting portion e.g. stem extending between the proximal and distal ends thereof. A portion of a mechanism for moving the or each movable window may extend through the connecting portion. The operator end may comprise one or more user interfaces e.g. a display, and one or more user interfaces for causing operation of the apparatus to move the or each movable window. These embodiments are particularly effective in testing a sample of fluid from an extracted sample. The operator end may house a set of one or more processors of the apparatus or unit, or other electronics thereof. The distal end of the apparatus or unit may provide an enlarged head portion to the apparatus which comprises the transmission cell. It is envisaged that in some embodiments, the or each movable window is confined to this head portion. The apparatus may be battery powered, although this need not be the case. The apparatus or unit may be a standalone apparatus or may be arranged to be connected to another device.

In other embodiments the apparatus is used to provide online testing of fluid in a system. The apparatus may be mounted with respect to the system such that fluid to be sampled enters the space between the first and second fixed walls in use. The fluid may be a flowing fluid. At least the transmission cell of the apparatus may be mounted so as to be immersed in a volume of fluid, such as a container or fluid conduit, within a system. The apparatus may be mounted such that the transmission cell is immersed in the fluid. In embodiments in which the apparatus is used in online testing, means e.g. a pump may be provided in the system to increase the flow of fluid in the region of the apparatus. This may help to provide a flow of fluid into the transmission cell. However, in other embodiments, the process flow of the system may itself be adequate. The movement of the movable window(s) may also help to draw fluid into the cell.

In preferred embodiments a source of electromagnetic radiation, the transmission cell and a detector of the apparatus are all located at a distal end of the apparatus or unit. The distal end of the apparatus or unit may then be immersed in a fluid to be sampled (whether in an online or extracted sample test). The apparatus or unit may be configured as an elongate probe having the transmission cell at the distal end thereof. This may enable the distal end to be dipped into fluid. In other embodiments, e.g. where the apparatus is used for online testing, other configurations may be appropriate. In either case, the source, transmission cell and detector may be located in a common housing.

The present invention is for use in performing measurements for use in the optical transmission analysis of a sample of fluid. The analysis may be to determine the presence and/or concentration of a substance or substances of interest in the fluid. The apparatus may or may not be arranged to perform the analysis using the measurements. In some embodiments, the apparatus may be arranged to output data indicative of the or each measurement performed on a sample for use in optical transmission analysis of the sample. The apparatus may be arranged to output such data in any suitable manner e.g. through wired or wireless transmission. Where the apparatus comprises a display, the display may be used to output the determined data. The data may then be processed remotely to perform the desired analysis of the sample e.g. to determine the presence and/or concentration of a substance of interest in the sample. Such arrangements may be particularly applicable where the apparatus is used for online testing. Alternatively, or additionally, the apparatus may be arranged to output data indicative of the or each measurement to a user. Alternatively, or additionally, the apparatus may be arranged to use the results of a measurement to generate data indicative of the presence or concentration of a substance of interest in the fluid. The apparatus may comprise a set of one or more processors for performing such a step. The apparatus may be arranged to output the determined data to a user. The apparatus may comprise a user interface for providing data indicative of the or each measurement performed and/or indicative of the presence or concentration of a substance of interest in the sample tested. The user interface may be a display. The user interface may be provided at a proximal end of the apparatus or unit where the transmission cell is located at a distal end thereof.

The apparatus may comprise a set of one or more processors. In some embodiments the movement of the first movable window (and any further movable window) is performed under the control of one or more processors. The movement may be initiated and/or driven under the control of the one or more processors.

The thickness of the first, or other, movable window refers to its extent in the direction between the first and second walls i.e. across the space defined between the walls.

A "window" as used herein refers to a region that is transparent to electromagnetic radiation of a wavelength or wavelengths with which the apparatus is intended to be used. In some embodiments a plurality of windows are provided e.g. in the second fixed wall, each of which acts as an optical filter to permit the passage of radiation of a given wavelength or wavelengths to a detector. Each such window may be arranged to pass a different wavelength or wavelengths of radiation.

The various windows of the apparatus may be made of the same or different materials. Using the same material for each window (both movable and fixed) is advantageous in that the windows will then have the same or at least similar thermal expansion coefficients to one another, reducing the impact of temperature variation on optical path through the sample, and hence on measurements. In general, the windows may be formed of any suitable optical window material or materials that is/are transparent at the wavelength(s) of interest. For example, suitable optical window materials may include calcium fluoride, sapphire, zinc selenide, fused silica and diamond. However, depending on the application and arrangement of the windows a wide range of other materials may suitably be used. For example, materials may be chosen depending upon the degree of robustness, resistance to scratching etc. required, as well as the type of fluid they are to contact.

The present invention extends to a method of using the sample testing apparatus in accordance with any of the aspects or embodiments of the invention to perform a measurement for use in optical transmission analysis of a fluid sample. The method may comprise, in any order, providing a fluid sample in the space between the first and second fixed walls, and operating the apparatus to cause the at least a portion of the first movable window to move into the test region. The method may further comprise introducing electromagnetic radiation through the window associated with the first fixed wall into the transmission cell, wherein the electromagnetic radiation follows an optical path through the sample comprising a portion extending through the or each gap between a one of the first and second fixed walls and the at least a portion of the first movable window, and detecting the electromagnetic radiation after passing along the path. The step of introducing the radiation is performed once the at least a portion of the first movable window is located in the test region.

In accordance with a further aspect of the invention there is provided a method of performing a measurement for use in optical transmission analysis of a fluid sample, the method comprising providing a sample testing apparatus, the apparatus comprising;

a transmission cell comprising first and second walls fixed in a spaced relationship relative to one another to define a space therebetween for receiving a fluid sample in use, at least the first wall being associated with a window, wherein electromagnetic radiation may be introduced through the window into the transmission cell in use for detection after passing through the sample;

the apparatus further comprising a first movable window, the first movable window being movable with respect to the first and second fixed walls, wherein the apparatus is operable to cause the first movable window to move with respect to the first and second fixed walls to move at least a portion of the first movable window into and out of a test region of the transmission cell, the test region being a region between the first and second fixed walls in the optical path of electromagnetic radiation introduced through the first fixed window into the transmission cell for passing through a fluid sample located in the space between the first and second fixed walls prior to detection in use;

wherein, when the at least a portion of the first movable window is located in the test region, a gap is defined between the at least a portion of the first movable window and one or both of the first and second fixed walls in the test region of the cell, such that an optical path is defined through a fluid sample in the cell for electromagnetic radiation introduced through the window associated with the first wall, the optical path through the sample comprising a portion extending through the or each gap between a one of the first and second fixed walls and the at least a portion of the first movable window;

the method comprising;

in any order, providing a fluid sample in the space between the first and second fixed walls, and operating the apparatus to cause the at least a portion of the first movable window to move into the test region. The method may further comprise introducing electromagnetic radiation through the window associated with the first fixed wall into the transmission cell, wherein the electromagnetic radiation follows an optical path through the sample in the test region comprising a portion extending through the or each gap between a one of the first and second fixed walls and the at least a portion of the first movable window, and detecting the electromagnetic radiation after passing along the path.

The present invention in these further aspects may include any or all of the features described in relation to the earlier aspects and embodiments of the invention, and may involve operating the apparatus in accordance with any of the methods described. The apparatus may be in accordance with any of the earlier described embodiments. Similarly, the apparatus of the earlier described embodiments may be arranged to be used in accordance with any of the aspects or embodiments of the methods described herein.

In these aspects and embodiments of the invention, the step of moving the at least a portion of the first movable window into the test region may be performed before, during or after the step of providing the fluid in the space between the first and second fixed walls. Preferably the step is carried out after the step of providing the fluid in the space between the walls. If the movement is carried out when fluid is already present in the transmission cell, the benefits in terms of a cleaning effect and renewal of the sample may be more readily obtained.

The method may further comprise operating the apparatus to cause the at least a portion of the first movable window to move out of the test region after the measurement has been performed.

The apparatus may be used to perform at least one further measurement of a fluid sample. The method may then comprise operating the apparatus to cause the at least a portion of the first movable window to move back into the test region, and introducing electromagnetic radiation through the at least a portion of the first movable window into the transmission cell, wherein the electromagnetic radiation follows an optical path through the fluid sample between the first and second fixed walls in the test region of the transmission cell, the path comprising a portion extending through the or each gap between a one of the first and second fixed walls and the at least a portion of the first movable window, and detecting the electromagnetic radiation after passing along the path to provide a further measurement.

The method may comprise using the or each measurement obtained in determining the concentration or presence of a substance in the fluid.

The method may further comprise operating the apparatus to cause the at least a portion of the first movable window to move into and out of the test region one or more times while fluid is provided between the first and second fixed walls and without introducing electromagnetic radiation into the transmission cell while the at least a portion of the window is in the test region. In other words, the window is moved into and out of the test region one or more further times without performing a measurement. This step may be performed before and/or after the, a, or each, step of operating the apparatus to cause the at least a portion of the first movable window to move into the test region and introducing electromagnetic radiation into the transmission cell and detecting the electromagnetic radiation to provide a measurement. The method may comprise then using the apparatus to perform measurement of a fluid sample once again i.e. using the steps of the method earlier described.

Operating the mechanism of the apparatus to move the first movable window into and out of the test region without performing a measurement may help to clean the optical surfaces of the windows, and to renew the sample for (further) measurement. The step of causing the first movable window to move so as to move the at least a portion thereof into and out of the test region may be carried out between any subsequent measurements taken, and may be performed once or multiple times between measurements. Such a step need not be performed after each measurement, but may be performed in place of full cleaning after a given number of successive measurements.

The method may comprise operating the apparatus to cause the first movable window to move from a non-test position to a test position in which the at least a portion thereof is located in the test region for performing the measurement, and to cause the first movable window to move back to the non-test position after performing the measurement. The first movable window may be moved directly back to the non-test position, or via a further position in which another portion thereof, or at least a portion of a second movable window is located in the or a test region. The various positions may be as described above.

The steps of operating the apparatus to cause the first movable window to move in any of the above manners may be initiated by the user i.e. through manual intervention or automatically as described above. The movement of the first movable window (or any further movable window) may be manually or automatically driven as discussed above.

Alternatively, or additionally, the method may comprise removing the transmission cell from contact with the test fluid, providing a cleaning fluid i.e. a different fluid, in the space between the first and second fixed walls, and operating the apparatus to cause the first movable window to move so as to move the at least a portion thereof into and out of the test region one or more times while the cleaning fluid is provided between the first and second fixed walls. This step is not a measurement step, and is carried out without introducing electromagnetic radiation into the transmission cell. The cleaning fluid may be of any suitable type, such as a solvent or a clean, light oil.

The step of providing fluid in the space between the first and second walls preferably comprises immersing the transmission cell of the apparatus in the fluid to be tested so that fluid enters the space. The transmission cell is preferably located at a distal end of the apparatus. The method may then comprise immersing the distal end of the apparatus in the fluid.

The apparatus may be used to test a sample of fluid from an extracted sample. The step of providing fluid in the space between the first and second walls preferably comprises immersing the transmission cell of the apparatus in the fluid to be tested so that fluid enters the space. The fluid to be tested may be held in any suitable container, such as a beaker etc. The transmission cell is preferably located at a distal end of the apparatus. The method may then comprise dipping the distal end of the apparatus in the fluid.

Alternatively, the apparatus may be used for online testing. The step of providing fluid in the space between the first and second fixed walls may then comprise mounting the apparatus with respect to a system using a fluid to be tested such that the fluid enters the space. The apparatus may be mounted such that at least the transmission cell is in the path of the flow of process fluid in the system. The apparatus may be mounted in any manner used for conventional flow through liquid transmission cells. The method may comprise mounting the apparatus with respect to a fluid conduit, such as a pipe, or within a fluid reservoir e.g. tank of a system. The movement of the first (or further) movable window in use may help to ensure that fluid enters the transmission cell of the apparatus effectively. Introducing test fluid to a liquid transmission cell may be challenging in view of the small dimensions often required to provide a suitable path length.

In embodiments in which the first movable window comprises first and second portions of different thickness, the at least a portion of the first movable window may be at least a portion of the first portion thereof. The method may further comprise operating the apparatus (before, or preferably after performing the measurement with the at least a portion of the first portion of the first movable window in the test region,) to move the first movable window so that at least a portion of the second portion of the first movable window moves into the test region, introducing electromagnetic radiation through the window associated with the first fixed wall into the transmission cell, wherein the electromagnetic radiation follows an optical path through the sample in the test region comprising a portion extending through the or each gap between a one of the first and second fixed walls and the at least a portion of the second portion of the first movable window, and detecting the electromagnetic radiation after passing along the path. In preferred embodiments the step is performed after performing the measurement with the at least a portion of the first portion of the first movable window in the test region, and comprises moving the first movable window so that the at least a portion of the first portion of the window moves out of the test region and the at least a portion of the second portion thereof moves into the test region. Thus a further measurement is taken with the path length through the sample being that obtained with the at least a portion of the second portion of the window located between the first and second fixed walls. The second portion of the first movable window is preferably thicker than the first portion thereof.

In embodiments in which the apparatus further comprises a second movable window, the method may further comprise operating the apparatus (before or preferably after performing the measurement with the at least a portion of the first movable window in the test region,) to move the second movable window so that at least a portion of the second movable window moves into the test region, introducing electromagnetic radiation through the window associated with the first fixed wall into the transmission cell, wherein the electromagnetic radiation follows an optical path through the sample in the test region comprising a portion extending through the or each gap between a one of the first and second fixed walls and the at least a portion of the second movable window, and detecting the electromagnetic radiation after passing along the path. In preferred embodiments the step is performed after performing the measurement with the at least a portion of the first movable window in the test region, and comprises moving the first movable window so that the at least a portion of the first movable window moves out of the test region. Thus a further measurement is taken with the path length through the sample being that obtained with at least a portion of the second movable window located between the first and second fixed walls. The second movable window, or the at least a portion thereof, is preferably thicker than the first movable window, or the at least a portion thereof.

The method may comprise causing the apparatus to perform a cycle as described in any of the above embodiments, in which respective portions of a window or windows are sequentially located in the test region.

However such measurements are obtained, the method may comprise using the measurements obtained based on the first and second portions of the first movable window, or based on first and second movable windows, in determining the concentration or presence of a substance in the fluid.

The fluid that is tested in accordance with the invention may be of any desired type. The fluid is preferably a liquid. In preferred embodiments the fluid is an oil. The oil may be an oil used in an engine, such as a marine engine. In such cases, the analysis may be performed to determine the presence and/or concentration of one or more contaminants or additives in the oil. In some embodiments the apparatus is used in determining the presence and/or concentration dissolved water in a sample of oil, or to determine a Total Base Number (TBN) of the oil. The method of the present invention may comprise using the apparatus in such a manner. The TBN of an oil is indicative of the reserve alkalinity of the oil, and is indicative of the remaining amount of additive present in the oil. The TBN may be indicative of the remaining amount of a substance which has been added to counter the acidity of the oil which may otherwise arise over time, due to the effects of corrosion etc. A TBN below a given threshold may indicate the necessity for an oil change.

Of course, the invention is applicable to testing a wide range of different fluids for a range of different substances. The skilled person will understand that different substances may be tested for by suitably selecting the wavelength of the radiation used, and selecting the path length through the fluid that is to be traveled by the radiation appropriately.

The electromagnetic radiation used in accordance with the invention may be of any suitable wavelength. It will be appreciated that depending upon the type of substance to be tested, different wavelengths will be more appropriate, corresponding to levels of greater absorption, and hence providing the ability to determine presence and/or concentrations of the substance of interest to greater degrees of accuracy. In preferred embodiments, the radiation is infrared radiation. However, the invention is not limited to radiation of this wavelength range, and may use radiation e.g. in the near red, visible or ultraviolet ranges of the electromagnetic spectrum. The most suitable wavelength must also be balanced with the path length that is provided by the transmission cell.

The methods in accordance with the present invention may be implemented at least partially using software e.g. computer programs. It will thus be seen that when viewed from further aspects the present invention provides computer software specifically adapted to carry out the methods herein described when installed on one or more data processors, a computer program element comprising computer software code portions for performing the methods herein described when the program element is run on one or more data processors, and a computer program comprising code adapted to perform all the steps of a method or of the methods herein described when the program is run on a data processing system. The one or more data processors may be a microprocessor system, a programmable FPGA (field programmable gate array), etc.

In embodiments in which a first movable window includes first and second portions of different thickness, with at least a portion of the first and second portions being respectively locatable in the test region, the at least a portion of the first or second portion may be only a portion thereof. This may be the case in particular where the first and second portions are separated by a stepped discontinuity. Where the first and second portions are provided by portions of a first movable window having a continuous variation in thickness, the first and second portions may be lines across the window. The at least a portion thereof may then be at least a portion of that line that is aligned with the test region. Likewise, the at least a portion of a second movable window that is locatable in the test region may be only a portion thereof. It is desirable that only a portion of the relevant portion or window is located in the test region to ensure that the relevant thickness portion or window extends over the test region to provide a predictable path length in the test region.

BRIEF DESCRIPTION OF THE DRAWINGS

Various embodiments of the present invention will now be described by way of example only, and by reference to the accompanying drawings in which:

FIG. 7 shows another sample testing apparatus for use in optical transmission analysis in accordance with the invention.

DETAILED DESCRIPTION

Figure 1:
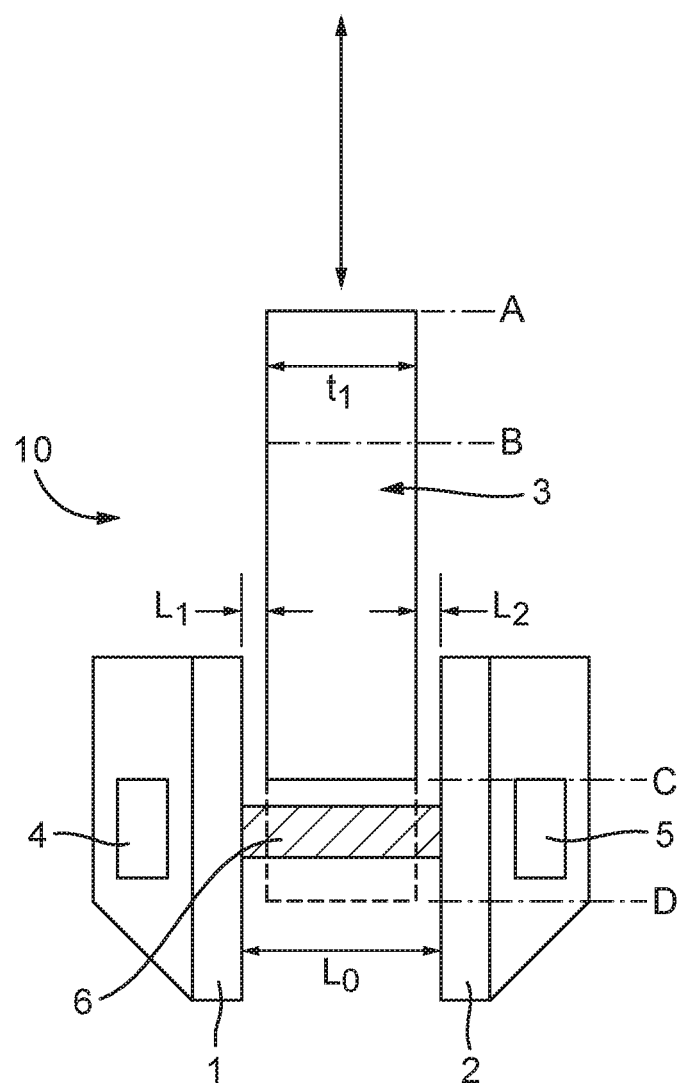
FIG. 1 schematically shows in vertical cross section showing the transmission cell and movable window of a sample testing apparatus in accordance with a first embodiment of the invention for use in optical transmission analysis.

The part of the sample testing apparatus 10 shown in FIG. 1 includes a transmission cell defined by a first fixed window 1 and a second fixed window 2. The windows 1, 2 are fixed in position relative to each other to define a space therebetween for receiving a fluid sample to be tested. It will be appreciated that when the transmission cell is immersed in fluid, fluid may enter the space around one or more the edges thereof. The testing apparatus 10 also includes a source of (e.g. infra-red) radiation 4 and a corresponding detector 5 for making measurements for use in performing optical transmission analysis of the fluid sample. The source of radiation may be a thermal source of broadband radiation, in certain preferred embodiments. The source 4 and detector 5 are housed in sealed compartments behind the first 1 and second 2 windows respectively, to prevent them coming into direct contact with the sample. The apparatus 10 further includes a first movable window 3 that is movable to move a portion thereof into and out of a test region 6 of the transmission cell defined in the space between the first and second fixed windows 1,2. The window 3 is movable in either direction of the arrow shown between a position in which the top edge and bottom edge of the window are at locations A and C respectively, and a test position in which the top and bottom edges are at the locations B and D respectively, such that a lower portion of the window is located in the test region. The position of the window when in the test region is indicated in dotted lines. The mechanism for moving the window is not shown in FIG. 1. The test region 6 is the region defined by the optical path of radiation travelling between the source 4 and the detector 5, and is indicated with hatched lines in FIG. 1. The test region is the region of the transmission cell, in which a measurement may be performed. The first movable window is arranged such that it is not moved to an extent that it completely leaves the transmission cell in order to move a portion thereof into and out of the test region. This is advantageous in that it enables the apparatus to be kept compact, and may avoid the need to guide the window. For example, a beam of radiation used might have a diameter in the order of 5-10 mm. This may then define the extent of the test region within the transmission cell e.g. the height and width thereof. The dimensions of the transmission cell are such that the height of the test region defined by the beam extends over only a portion of the height of the cell, and typically the width of the test region extends over only a portion of the width of the cell.

It will be appreciated that although the source 4 and detector 5 are illustrated in FIG. 1 (and in all of the following figures) as being on opposite sides of the transmission cell, this is not necessarily the case and for instance the second fixed window may be replaced with a fixed wall carrying a mirror for reflecting the radiation towards a detector mounted behind the first fixed window 1, thus effectively doubling the optical path length. There may also be multiple detectors or detecting regions associated with i.e. provided on or behind either of the first fixed window or the second fixed window/wall. For instance, whilst the detector 5 in FIG. 1 is illustrated as a single component, the detector 5 may include a number of apertures associated with different (e.g. infra-red) filters that define the measured wavelengths, and it is only the parts of the beam incident upon these apertures that are measured. Naturally in this case the diameter of the beam must be wide enough to illuminate each of the apertures of the detector. Typically, each aperture and an associated optical filter is located behind the applicable fixed window so that the window may seal each aperture from the fluid, although it is envisaged that the window could instead include multiple windows, each providing a filter for an aperture of the detector. Various suitable configurations of the source and detector will be apparent to a person skilled in the art. As is known in the art, the intensity of the source 4 may be modulated, with only the signal at the modulation frequency being amplified and measured in order to reject drift or off-frequency noise associated with e.g. the electronics of the detector 5.

When the movable window 3 is retracted, i.e. is positioned in the upper position with its edges at positions A and C respectively such that the entire window is located outside of the test region as shown in FIG. 1, an optical path between the source 4 and the detector 5 is defined through the first and second windows 1, 2 and the space defined therebetween. The retracted position may be referred to as a non-test position. If a sample fluid is introduced into the transmission cell with the movable window 3 retracted, the optical path length through the sample is the distance between the first and second windows, i.e. $L_0$.

When the movable window 3 is moved to the position indicated in dotted lines with the upper and lower edges thereof at positions B and D respectively, so as to dispose a portion thereof in the test region, with the positioned in-line between the source 4 and the detector 5 in the test region, the sample fluid within the transmission cell will be displaced so that it is confined to the gaps $L_1$, $L_2$ between the first fixed window 1 and one side of the portion of the first movable window 3 (i.e. $L_1$) and between the other side of the first movable window 3 and the second fixed window (i.e. $L_2$). Accordingly, when the movable window 3 is moved so as to dispose a portion thereof in the test region, the optical path length in the test region through the sample fluid for the optical transmission measurement is reduced from $L_0$ to $L_1+L_2$.

Although FIG. 1 shows symmetrical gaps formed on either side of the first movable window 3 ($L_1=L_2$), this is not necessary and the first movable window 3 may be offset towards either of the first or second fixed windows or may even ride along the first or second fixed window, with just enough clearance to avoid the mechanism jamming. Indeed, it does not particularly matter what fraction of the path is provided on either side of the first movable window 3 when in the test position, so long as the total path length ($L_1+L_2$) through the sample is fixed. As the path length is fixed by the thickness $t_1$ of the first movable window 3 and the width of the space between the first and second fixed windows $L_0$, the mechanism for moving the first movable window 3 need not be particularly precise.

It will be appreciated that the thickness of the movable window $t_1$ may be selected to be arbitrarily close to the distance between the fixed windows, $L_0$, so that arbitrarily short path lengths, i.e. $L_1+L_2=L_0-t_1$, can be provided.

Where the sample testing apparatus 10 is used for infra-red optical transmission measurements on liquids, for example, oils, the path length through the sample needs to be relatively short otherwise the radiation will largely be absorbed before reaching the detector so that insufficient power will be received at the detector 5 to accurately measure the signal. However, there is a trade-off here, and the path length cannot be too short otherwise any changes in detected power due to different concentrations may become too small to be detected relative to the noise introduced by the infra-red source and measurement circuit. It has been found that path lengths on the order of around 0.05 to 0.2 mm are suitable for many liquid measurements, although path lengths outside this range may also be used, and may even be more suitable for some liquids. Typical applications of the sample testing apparatuses described herein, for which this order path length may be suitable, include the measurement of dissolved water content or total base number (TBN) in lubricating oils. However, it will be appreciated that the sample testing apparatus 10 is not limited to these applications, or indeed these path lengths, and is generally suited for any transmission measurements. For instance, the sample testing apparatus 10 may also suitably be used to determine the presence or concentration of many different types of chemical substances in a variety of fluids. Generally, the path length must be determined to at least the same accuracy that it is desired to measure the concentration with, so, for example, to determine a concentration to +/−5% with a 0.1 mm path length, the path length must be fixed to better than +/−5 micrometres. Thus, it is important that the path length can be fixed accurately, e.g. so that it doesn't change after any initial calibration, and also that the surfaces defining the path length are clear of contaminants.

To achieve a path length through the sample, i.e. the gap(s) between the movable window 3 and the fixed windows 1, 2 of the order 0.05 to 0.1 mm, the thickness $t_1$ of the movable window must be around 0.05 to 0.1 mm less than the distance between the first and second fixed windows, i.e. $L_0$. To give an idea of scale, in a practical embodiment for use with infrared radiation, the spacing between the first and second 1, 2 windows, $L_0$, may be around 2-3 mm. However, it will be appreciated that the spacing between the first and second windows is not particularly important, so long as a suitably thick movable window is provided, and what matters is the difference $L_0-t_1$, that defines the size of the gaps, i.e. $L_1$ and $L_2$, and hence the path length $L_1+L_2$.

Generally, a spacer may be provided between the fixed windows 1, 2 to determine the separation, $L_0$, between them. For practical reasons, to ensure that the path through the sample fluid does not vary excessively with temperature, the spacer may advantageously be formed from the same material as the fixed windows 1, 2 and the movable window 3. The spacer may, for example, include a suitably dimensioned piece of material. The spacer may further, or alternatively, comprise glass microspheres mixed with adhesive. By selecting microspheres having suitable diameters, a precise fixed spacing between the first 1 and second 2 windows may be obtained. It is envisaged that glass microspheres may be used to provide fine adjustment of a gap provided by a piece of spacer material. For conventional transmission cells having relatively short path lengths, e.g. of the order 0.1 mm, it can be difficult to introduce test fluid into the test region, and even more so to adequately clean the cell afterwards. This is especially the case where the fluid is relatively viscous or dirty as would be the case for lubricating oils. It can thus be very time consuming to clean such a cell, and if the cell is not adequately cleaned, the contamination may significantly affect future measurements.

It will be appreciated that the apparatus of the present invention is much improved in this respect due to the presence of the movable window. For instance, for the apparatus 10 shown in FIG. 1, when the first movable window 3 is retracted from the test region, there is a relatively large space provided between the first and second windows into which a sample can easily be introduced and subsequently removed/cleaned. Furthermore, the action of moving the portion of the movable window 3 into the test region may itself help to remove the sample and facilitate cleaning of the transmission cell. The movement of the window to move the portion thereof into and out of the test region will act to clean the optical surfaces of the fixed and movable windows through the movement of fluid caused, and may be carried out one or more times to provide a cleaning step between measurements, and help to remove traces of a previous sample. This avoids the need to use any special cleaning fluids between every measurement. However, on some occasions, to provide more thorough cleaning of the transmission cell, the sample testing apparatus 10 may be inserted into a beaker of solvent or lighter cleaner oil, and the movable window 3 may be retracted, or repeatedly actuated in and out of the test region in order to remove traces of the previous sample. It has been found that the amount of movement of the movable window required to provide these advantages may be minimal. Provided that there is some movement in order to move at least a portion of the window into or out of the test region, benefits will be obtained in terms of promoting fluid exchange within the transmission cell, and cleaning of the cell between measurements.

Operating the movable window 3 therefore serves both to position it for a measurement and to drive the exchange of fluid within the cell for measuring new samples and/or for cleaning the cell. Thus, it will be appreciated that the sample testing apparatus 10 of the present invention can be cleaned relatively quickly and easily whilst still providing the required short path lengths for optical transmission measurements. This makes it particularly advantageous for use in a field setting, rather than a laboratory, where it is desirable to be able to rapidly perform measurements, without needing to disassemble the apparatus between measurements for cleaning.

It is envisaged that the apparatus may be configured to enable the first movable window to be moved to a maintenance position e.g. for specific cleaning or servicing, in which it is fully outside the transmission cell.

In the apparatus illustrated in FIG. 1, the movable window 3 may be slid linearly relative to the first 1 and second 2 fixed windows to move the portion thereof into and out of the test region. However, any suitable mechanism for moving the movable window 3 may be employed, and it is also contemplated for instance that the first movable window 3 may be swung in from a side, or mounted on a rotatable carrier. In any of these cases, the mechanism for actuating the first movable window 3 can be manually operated or controlled electrically. For instance, where the first movable window 3 is manually actuated, it may conveniently be slid linearly in and out of the space between the first and second fixed windows via a spring loaded pushrod operated by thumb pressure, or alternatively swung in from the side on the end of a sprung lever operated by the user squeezing a grip. Naturally, there are various other ways in which the first movable window 3 may be moved between the two fixed windows 1, 2 that will be apparent to the skilled person. It will be appreciated that the mechanism for moving the movable window, or the way in which it is mounted relative to the transmission cell, is not shown in FIG. 1.

The movable window 3 shown in FIG. 1 is of essentially cuboidal shape and constant thickness $t_1$.

It will be appreciated that the extent of the test region may vary. Rather than being an extended region e.g. defined by the width of a beam of the electromagnetic radiation, the test region may be defined by a line along which the radiation passes between the source and detector. Furthermore, the first movable window may be movable to a greater or lesser extent in order to move a portion thereof into or out of the test region. The movement may be a movement in which the entire window remains within the space between the first and second fixed windows, or may be a movement in which the entire window moves out of the space when in the retracted position.

Figure 2:
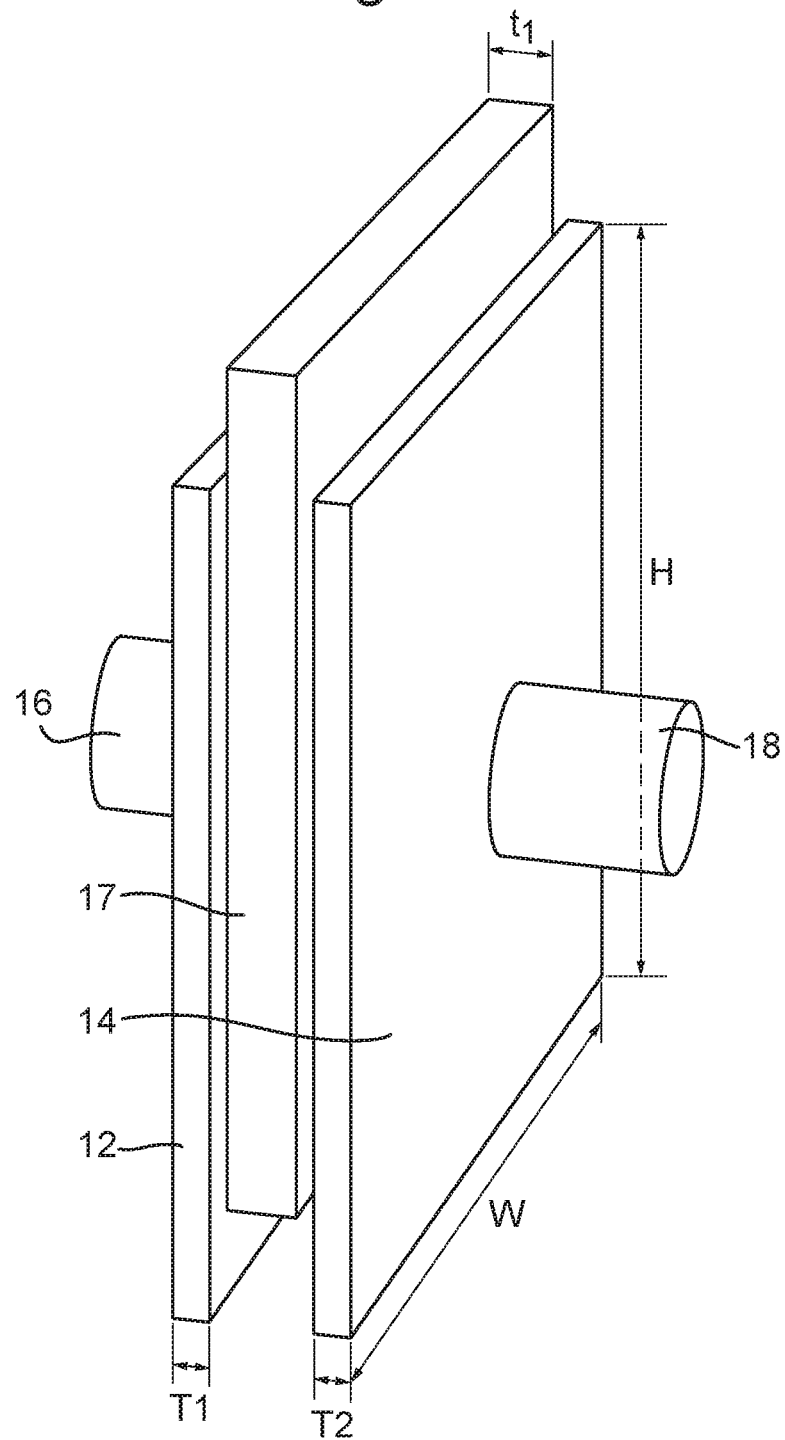
FIG. 2 is a perspective schematic view of a transmission cell and movable window of a sample testing apparatus in accordance with an embodiment the invention.

FIG. 2 is a schematic perspective view of a portion of a sample testing apparatus similar to that shown in FIG. 1 in the region of the transmission cell. The transmission cell is defined by first and second fixed windows 12, 14, behind which a source 16 of electromagnetic radiation and a detector 18 are located. A first movable window 17 is movable between the first and second fixed windows to align a portion thereof with the test region defined in the transmission cell. The mechanism for moving the window is not shown. The fixed windows have a width W and a height H along the directions marked. The first fixed window 12 has a thickness $T_1$, and the second fixed window 14 has a thickness $T_2$. The thickness of the movable window 17 is $t_1$.

Figure 3:
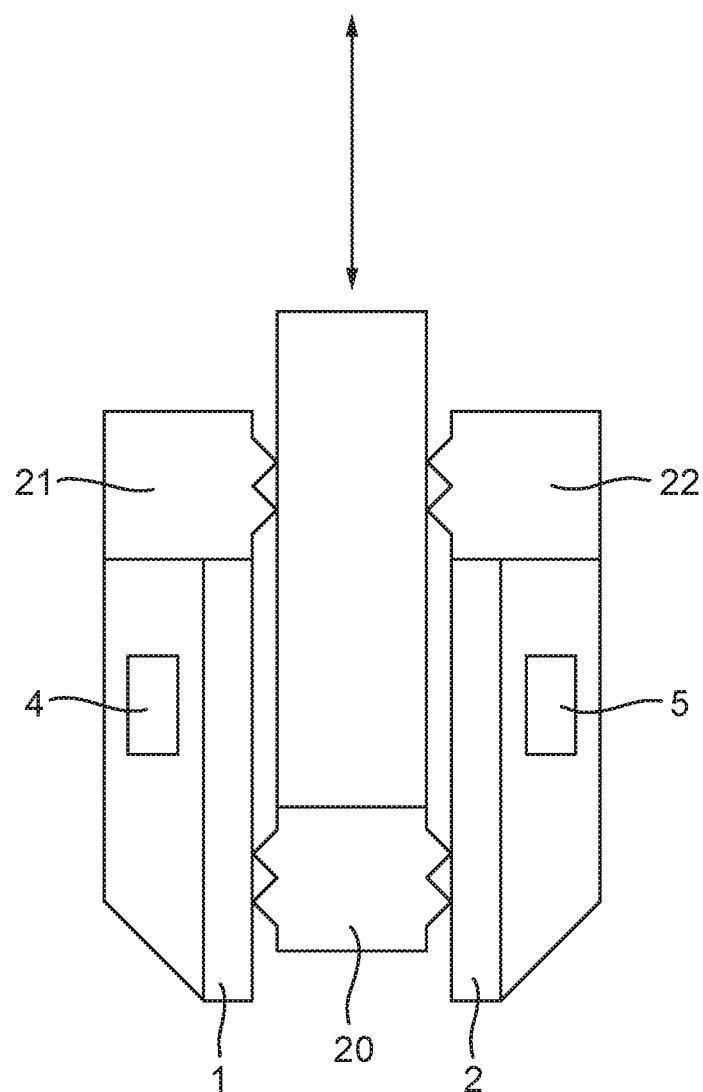
FIG. 3 schematically shows in vertical cross section of the transmission cell and movable window of a sample testing apparatus in accordance with another embodiment of the invention for use in optical transmission analysis, and which includes wipers.

In some preferred embodiments, to further facilitate cleaning of the transmission cell, compliant wipers may be provided for wiping the sample contacting surfaces of the first and second windows 1, 2 and/or the movable window 3. One suitable arrangement is shown in FIG. 3. Like components have the same numbering as in FIG. 1. The sample testing apparatus shown in FIG. 3 is similar to that of FIG. 1, except that a compliant wiper 20 is provided on the leading end of the movable window, and compliant wipers 21, 22 are also provided at the top end of both of the first and second windows 1, 2. The wipers are arranged so that each of the optical surfaces exposed to the sample fluid, i.e. the surfaces of the first and second fixed windows that define the transmission cell and both surfaces of the movable window are wiped clean as the movable window 3 is moved to move the portion thereof into and out of the test region. The compliant wipers 20, 21, 22 may for example be formed of rubber, or any other suitably compliant material. The use of such wipers may further reduce the need for a separate cleaning action (e.g. using a solvent) between measurements, as the transmission cell is cleaned every time the mechanism is operated and the volume of new liquid within which it is immersed may be sufficient to remove and dilute any traces of the previous liquid. The wipers may also, e.g. when disposed as in FIG. 3, act to limit movement of the movable window relative to the first and second fixed windows, e.g. to prevent the window from being completely removed from the transmission cell, although the wipers do not need to provide this further function. Although not always illustrated, it will be appreciated that such wipers may similarly be provided in each of the embodiments described herein, for wiping the surfaces of the or each movable window or window portion and the first and second fixed windows, and advantageously limiting movement of movable window(s). In particular, it will be understood that the use of wipers are not limited to embodiments where the movable window is linearly slid into the test region. The wipers need not extend across the full width of the window(s), provided that they are arranged to wipe at least the portion of the window(s) that will be aligned with the test region when performing measurements. For example, the wipers may be confined to a centre portion of the width of the movable and fixed windows, corresponding to a portion through which the radiation will travel between the source and detector e.g. where the source and detector are located in a similar manner to that shown in FIG. 3.

It will be appreciated that the size of the gap(s) between the first movable window 3 and the first 1 and second 2 fixed windows, at least in relation to the portion of the window that is to be disposed in the test region, is of critical importance to the measurement and must be accurately controlled. In some circumstances it may therefore be preferable to obtain a differential measurement using two different thickness portions of a movable window or two movable windows of different thickness. The two different portions or windows may each be moved into the test region to enable two measurements of the transmission through the sample to be obtained. This is generally beneficial to measurement accuracy as it may remove the dependence on the intensity of the source, provided that the first and second measurements are taken at close enough times (so as to avoid drift as the source warms up). This is especially valuable when making quick measurements with a portable instrument as the emitted power of typical infra-red sources is strongly dependent on temperature (of the order of the $4^{th}$ power of the absolute temperature (in K)) and such sources may take a significant time to reach a stable temperature, and may consume too much power to be left permanently on e.g. in a battery-powered instrument. Furthermore, the length of the measurement path is inherently well compensated for temperature variations since both portions or windows can be made from the same material and will typically only differ very slightly in thickness.

Figure 4:
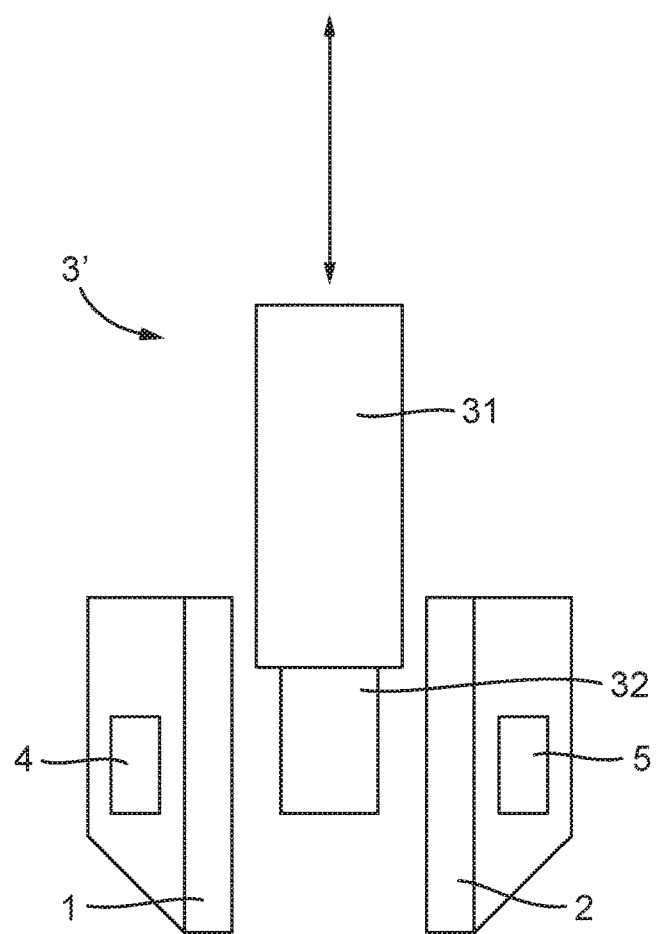
FIG. 4 schematically shows in vertical cross section the transmission cell and movable window of a sample testing apparatus in accordance with another embodiment of the invention for use in optical transmission analysis in which the movable window includes portions of different thickness.

For instance, FIG. 4 is a vertical cross sectional view through another sample testing apparatus in the region of the transmission cell, like FIG. 1. The components of this embodiment which correspond to those of FIG. 1 have like reference numerals. The difference is that in the embodiment of FIG. 4, the movable window 3' includes two different thickness portions 31, 32. The movable window 3' therefore has a stepped discontinuity in thickness. The movable window 3' may then be moved between a retracted position e.g. a non-test position, a first test position where a portion of the reduced thickness portion 32 is positioned in-line between the source and the detector in the test region, and a second test position where a portion of the thicker portion 31 is positioned in the test region. The infra-red absorption may thus be determined as the difference between the signal measured at the first and second test positions, i.e.:

$$\log(I_{thick}) - \log(I_{thin}) = [\log(I_0) - \alpha \cdot c \cdot L_{thick}] - [\log(I_0) - \alpha \cdot c \cdot L_{thin}] = \alpha \cdot C \cdot (L_{thick} - L_{thin})$$

where $I_{thick/thin}$ is the measured intensity at the second/first test positions, $I_0$ is the source intensity, $\alpha$ is the absorption co-efficient of the sample, c is the concentration of the sample and $L_{thick/thin}$ is the path length at the second/first test position, defined respectively by the gaps between the portions of the window 31, 32 and the fixed first and second windows when disposed in the respective test position.

The measurement path thus corresponds to the difference in thickness between the two portions 31, 32. For instance, for a measurement path of 0.1 mm, the first portion 32 may have a thickness of 1.9 mm and the second portion 31 a thickness of 2.0 mm. The gap between the fixed first and second windows and the first movable window 3 is now no longer critical, and need only just be sufficient to ensure that the mechanism doesn't jam. It may be convenient therefore to have the thicker portion 31 mounted so that it compliantly rides on the surfaces of the fixed windows 1, 2. Again, it will be appreciated that the thicknesses of the first and second portions 31, 32 relative to the spacing between the fixed windows may be selected arbitrarily to define a particular path length, suitable for any given application, and the numbers presented above are merely for illustrative purposes.

Figure 5:
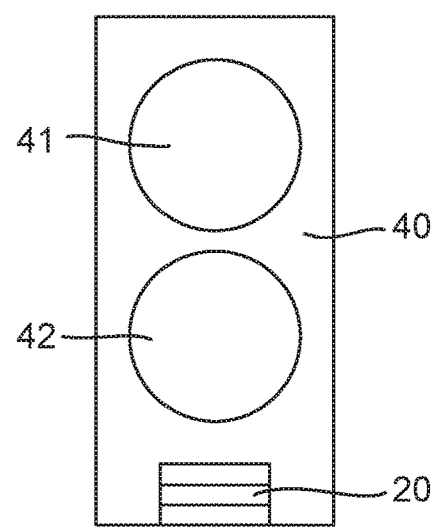
FIG. 5 schematically shows in vertical cross section a window carrier having first and second movable windows of different thickness mounted thereto for use in accordance with some further embodiments of the invention.

Another exemplary movable window arrangement for a sample testing apparatus in accordance with the invention for obtaining differential measurements is shown in FIG. 5. Here, a window carrier 40 is provided containing a first movable window 41 and a second movable window 42 of different thickness. The carrier is mounted with respect to a transmission cell such that the carrier is movable relative to the first and second fixed windows 1, 2 in the space defined therebetween in a similar manner that the movable window 3 is mounted e.g. in FIG. 3. In this way, both the first and second movable windows 41, 42 are movable relative to the fixed windows 1, 2, although are not movable relative to one another. The carrier may replace the single movable window shown in FIG. 1, for example. The apparatus is operable to move at least a portion of either the first or second windows into the test region for performing the transmission measurement. The carrier may be moved to a first test position in which at least a portion of the first movable window is in the test region, or a second test position in which at least a portion of the second movable window is in the test region. The carrier of FIG. 5 also contains a compliant wiper 20, similar to those described above in relation to FIG. 3. Other types of carrier may be envisaged e.g. a rotatable carrier having multiple arms, each having one of the respective first and second movable windows thereon.

An alternative to having a single movable window defining two portions of distinct and different thickness, or a single movable carrier having two windows of distinct and different thickness as shown in FIGS. 4 and 5 would be to have a single movable window with a wedge angle. However, in this case, the position of the wedge between the first and second fixed windows would need to be determined accurately to determine the path length when the relevant portion of the movable window is disposed in the test region, so this may be less convenient.

It is noted that it is also known in the art to use a small wedge angle to reduce the effect of reflections. This may also be done in embodiments of the present invention, but it is preferably done on the fixed windows (only). If a wedge is provided on the movable window for this reason, preferably the wedge is not provided in the direction of movement. In any case, the wedge angle should be small enough so as to not significantly interfere with the determination of the optical path length.

Figure 6:
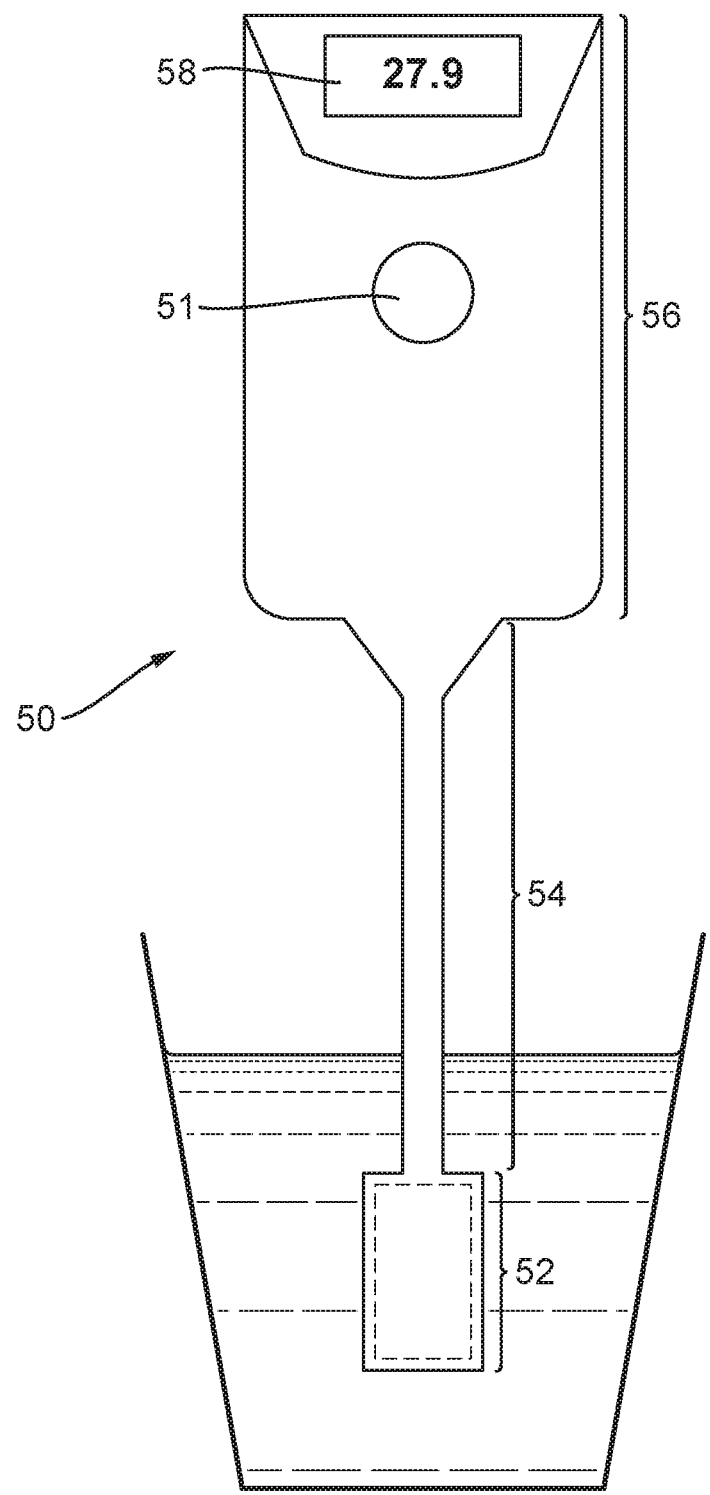
FIG. 6 shows an exemplary sample testing unit including a sample testing apparatus for use in optical transmission analysis in accordance with the present invention.

FIG. 6 shows an exemplary handheld sample testing unit 50 including a sample testing apparatus 10 of any of the types described above. The part of the sample testing apparatus as shown in e.g. FIGS. 1-4, including the transmission cell and the movable window(s), is provided at the enlarged distal end 52 of the instrument, at the end of a probe part thereof in the dotted region indicated. The probe portion is configured to allow fluid to enter the distal end of the unit, and hence enter the transmission cell. For example, the bottom face of the distal end may be open. The movement of the movable window(s) is confined to this distal end 52 of the unit. The actuation of the sample testing apparatus, i.e. the movement of the movable window(s) into and out of the test region is controlled manually by a button 51 on an operator portion at the proximal end 56 of the apparatus. This may be connected e.g. using a push rod or other mechanism extending through a stem 54 of the unit to the movable window. Wires for transmitting data from the transmission cell to one or more processors in the proximal end of the apparatus may extend through the stem. The distal end may include any components that need to be located close to the transmission cell e.g. pre-amplifiers. The apparatus also includes a display 58 for outputting the result of the measurement to a user. The apparatus is battery operated. A battery may be located at the proximal end 56. Of course, in other embodiments the apparatus need not be battery operated. For example, the apparatus may be connected e.g. via a cable to another device. The apparatus may then be powered by the other device. Other functionality of the proximal end of the unit shown in FIG. 6 may then be provided by the device e.g. a display, some processing etc.

In use, the probe part of the unit may be immersed into a beaker of sample fluid so that the space between the first and second fixed windows of the transmission cell of the sample testing apparatus is flooded with sample fluid. The unit is then actuated to move the or a movable window into a test position in which at least a portion thereof is located in the test region, and an infra-red transmission measurement is then obtained. As described above, the act of actuating the unit to move the movable window displaces much of the fluid from the cell, other than in the gaps provided between the movable window and the fixed windows. Where the sample testing apparatus contains a movable window having two portions of different thicknesses as shown in FIG. 4, the unit may be actuated to move the movable window sequentially into first and second test positions, in which at least a portion of the first portion and at least a portion of the second portion thereof are respectively disposed in the test region. In embodiments as shown in FIG. 5 in which two movable windows are provided, at least a portion of the first and second movable windows may be located sequentially in the test region. This may be achieved by actuating the unit to move the carrier between a first test position in which at least a portion of the first movable window is in the test position, and a second test position in which at least a portion of the second movable window is in the test region. The user may or may not need to press the button again after initial actuation to move the different portions of a window, or different windows into the test region. Operation of the source to perform a measurement may occur automatically when the relevant window or portion thereof is in the test region, or may require user intervention. After the measurement(s) are obtained in each test position, the unit may be removed from the sample, or actuated again one or more times, in order to clean the cell for measurement of a new sample.

Alternatively, instead of a user manually actuating the unit e.g. using a button as shown in FIG. 6, the unit can be electronically actuated so that the movable window (and any further movable window) is rapidly driven between the various positions. This may be achieved by driving a window carrier to which the window(s) are mounted. This may be particularly beneficial for use with sample testing apparatuses like those shown in FIG. 4 or 5 in which a window or window carrier may be moved between multiple test positions. The movable window(s) can thus be rapidly, automatically driven to dispose them, or different portions thereof, in the test region i.e. between the various test positions. This may replace the usual modulation of the source and help to more effectively cancel any drift in the measurements due to the source warming up. An additional benefit of rapidly driving the window(s) is that this movement may help to agitate and mix the fluid being measured. This may be particularly useful in the case of infra-red measurements of water in oil where a limiting factor in the determination of water content at high water contents is the tendency of water to separate out into droplets. Operation of the source to perform a measurement may occur automatically when the relevant window or portion thereof is in the test region.

In alternative embodiments, rather than being arranged for extracted sample testing, the apparatus may be configured to be used for online or flow through testing. In these embodiments, the apparatus or a sample testing unit including the apparatus, is mounted with respect to a fluid containing system so that fluid from the system enters the transmission cell. Thus, the apparatus is mounted with the transmission cell immersed in fluid. The apparatus may be of any suitable configuration in these embodiments.

Another exemplary sample testing apparatus will be described by reference to FIG. 7. FIG. 7 is a front on view of the apparatus showing the interaction between a movable window and the transmission cell thereof. The sample testing apparatus includes two fixed windows that define a transmission cell having a test region as in the earlier embodiments. In the embodiment illustrated in FIG. 7, a movable window 60 is arranged to rotate or be rotated in a plane parallel to the fixed windows so that the first 61 and second 62 ends of the movable window are alternately rotated into the test region 64 between the source and the detector (not shown in FIG. 7). One of the fixed windows, 63, is shown in FIG. 7. The first and second ends 61, 62 may generally be of the same thickness, or may be of different thicknesses in a similar manner to what is described above in relation to FIGS. 4 and 5. In the embodiment illustrated in FIG. 7, the movable window(s) form part of a rotor, the rotor being defined by the windows. However, it will be appreciated that the movable window(s) may alternatively be provided on a rotatable carrier.

In other embodiments one of the ends of the rotor defined by the movable window(s) or rotatable carrier may simply comprise a compliant wiper for cleaning the transmission cell between measurements. Also, although the window shown in FIG. 7 only has two ends, it is contemplated that a rotor defined by the movable window(s) or rotatable carrier may have multiple 'ends' each of which may comprise a window and/or a compliant wiper. For example, the rotor defined by the movable window(s) or rotatable carrier may be in the form of a cross with four end portions that are alternately rotated through the test region.

In any case, whatever its configuration, it will be appreciated that the or part of the rotating window or window carrier may act as an impeller to draw sample fluid into the test region. The apparatus shown in FIG. 7 may thus be particularly suitable for performing in-line measurements within a tank of sample fluid or within a flow of sample fluid, and may be provided as part of a sample testing unit for these applications. This type of sample testing unit may generally be referred to as a 'flow cell'. For example, the sample testing apparatus of FIG. 7 may be disposed within a large tank of sample fluid and the rotating member may be automatically (or manually) rotated so that the end portions 61, 62 are alternately moved into the test region for obtaining optical transmission measurements of the sample. As the rotating member rotates to move the next end portion into the test region, it will drive sample fluid out of the test region and draw new sample fluid in for the next measurement. In conventional flow cells, where the fluid ingress is driven by a pump or the process pressure, it can be difficult to push viscous fluids through the relatively small gap defining the optical path. This may limit the achievable flow rate and hence measurement frequency. However, where a movable window is used, e.g. as shown in FIG. 7, when the movable window is outside of the test region, so that the gap between the fixed windows is relatively large, sample fluid can be driven in at relatively high flow rates, before the window is rotated back into the test region to reduce the gap (i.e. optical path length) for a measurement. Thus, using a rotatable window may help to facilitate improved sample throughput for on-line measurements. In other embodiments, such arrangements may use a rotatable carrier. Of course, similar advantages may be obtained in any of the embodiments of the invention, in that a movable window is moved into and out of a test region of the transmission cell, and online type embodiments need not use rotational arrangements.

Although the present invention has been described with reference to particular embodiments, it will be understood by those skilled in the art that various changes in form and detail may be made without departing from the scope of the invention as set forth in the accompanying claims. Particularly, it will be appreciated that features described in relation to particular embodiments or for use in particular preferred applications may also be applied to other embodiments, except where these are mutually exclusive. For instance, any dimensions listed above are merely illustrative and whilst suitable for some preferred applications, the skilled person will appreciate that the relative dimensions of the various windows and gaps can be changed as desired for a given application.

The invention claimed is:

1. A sample testing apparatus for use in optical transmission analysis of a fluid sample, the apparatus comprising;
   a transmission cell comprising first and second walls fixed in a spaced relationship relative to one another to define a space therebetween for receiving a fluid sample in use, at least the first wall being associated with a first fixed window, wherein electromagnetic radiation can be introduced through the first fixed window into an optical path in the transmission cell in use for detection after passing through the sample;
   the apparatus further comprising a first movable window, the first movable window being movable with respect to the first and second fixed walls, wherein the apparatus is operable to cause the first movable window to move with respect to the first and second fixed walls to move at least a portion of the first movable window into and out of a test region of the transmission cell, the test region being a region between the first and second fixed walls in the optical path of electromagnetic radiation introduced through the first fixed window into the transmission cell for passing through a fluid sample located in the space between the first and second fixed walls prior to detection in use;
   wherein, when the at least a portion of the first movable window is located in the test region, a gap is defined between the at least a portion of the first movable window and one or both of the first and second fixed walls in the test region of the cell, such that the optical path has a length of up to 1000 micrometres defined through a fluid sample in the cell for electromagnetic radiation introduced through the first fixed window associated with the first wall, the optical path through the sample comprising a portion extending through the or each gap between a one of the first and second fixed walls and the at least a portion of the first movable window, and
   the apparatus further comprising a set of one or more wipers for wiping one or both of the sample fluid contacting surfaces of the first movable window during relative movement between the first movable window and the first fixed and second fixed walls and/or for wiping the sample contacting surface of the or each first fixed window associated with the first and second fixed walls of the apparatus during relative movement between the first movable window and the first and second fixed walls.

2. The sample testing apparatus of claim 1, wherein when the at least a portion of the first movable window is located in the test region, the optical path defined through the fluid sample is less than 500 micrometres, optionally wherein the optical path is less than 250 micrometres.

3. The sample testing apparatus of claim 1, wherein the space between the first and second fixed walls in the test region has a width of at least 1 mm.

4. The sample testing apparatus of claim 1, wherein the first movable window is movable relative to the first and second walls between a non-test position and a test position in which the at least a portion thereof is disposed in the test region.

5. The sample testing apparatus of claim 4, wherein the non-test position is a position in which no portion of the first movable window is located in the test region.

6. The sample testing apparatus of claim 1, wherein movement of the first movable window to bring the at least a portion of the first movable window into or out of the test region is a movement in which the at least a portion of the first movable window remains within the transmission cell.

7. The sample testing apparatus of claim 1, when the at least a portion of the first movable window is located in the test region between the first and second fixed walls, a first gap is defined between the first fixed wall and the at least a portion of the first movable window in the test region, and a second gap is defined between the portion of the first movable window and the second fixed wall, wherein the optical path defined through the sample between the first and second fixed walls for electromagnetic radiation introduced through the window of the first wall in the test region comprises a portion extending through the first gap, and a portion extending through the second gap.

8. The sample testing apparatus of claim 1, further comprising a source of electromagnetic radiation arranged to introduce electromagnetic radiation into the transmission cell through the first fixed window of the first fixed wall into the test region in use, and a detector for detecting radiation after passing through the test region of the cell.

9. The sample testing apparatus of claim 8, wherein the second fixed wall is associated with at least one first fixed window, and the detector is located behind the at least one first fixed window for detecting radiation after passing through the cell.

10. The sample testing apparatus of claim 1, wherein the transmission cell is bounded by first and second fixed windows on either side thereof, the fixed windows providing respectively the first and second fixed walls.

11. The sample testing apparatus of claim 1, wherein the apparatus is configured such that fluid can enter the space between the first and second walls when the transmission cell is immersed in fluid.

12. The sample testing apparatus of claim 11, wherein the apparatus is configured such that fluid can enter the space along at least one edge of the space when the transmission cell is immersed in fluid.

13. The sample testing apparatus of claim 11, wherein the first movable window is mounted to a window carrier, the window carrier being movable to cause movement of the first movable window.

14. The sample testing apparatus of claim 1, wherein the first movable window is linearly movable.

15. The sample testing apparatus of claim 1, wherein the first movable window is rotationally movable.

16. The sample testing apparatus of claim 1, wherein movement of the first movable window is initiated automatically or in response to one or more actions by a user.

17. The sample testing apparatus of claim 1, wherein movement of the first movable window is driven automatically, or manually by a user.

18. The sample testing apparatus of claim 1, wherein the apparatus includes a single window movable relative to the first and second walls.

19. The sample testing apparatus of claim 1, wherein the first movable window comprises first and second portions of different thickness, the at least a portion of the first movable window being at least a portion of the first portion thereof, wherein the apparatus is operable to cause the first movable window to move relative to the first and second fixed walls to move at least a portion of the second portion of the first movable window into and out of the test region.

20. The sample testing apparatus of claim 19, wherein the apparatus is operable to perform a cycle in which the first movable window is moved to locate at least a portion of the first portion and at least a portion of the second portion of the first moveable window sequentially in the test region in any order for performing respective measurements.

21. The sample testing apparatus of claim 19, wherein the first movable window varies continuously in thickness, or wherein the first movable window has a stepped variation in thickness.

22. The sample testing apparatus of claim 19, wherein the first movable window is movable between at least a first position relative to the fixed walls in which at least a portion of the first portion thereof is located in the test region and a second position in which at least a portion of the second portion thereof is located in the test region, and preferably a third position in which no portion of the first movable window is located in the test region.

23. The sample testing apparatus of claim 19, wherein, when the at least a portion of the first portion of the first movable window is located in the test region, an optical path of a first length is defined through the sample in the test region between the first and second fixed walls for electromagnetic radiation introduced through the window of the first fixed wall, and when the at least a portion of the second portion of the first movable window is located in the test region, an optical path of a second length is defined through the sample between the first and second fixed walls in the test region for electromagnetic radiation introduced through the first fixed window of the first fixed wall, the first and second path lengths being different.

24. The sample testing apparatus of claim 1, wherein the apparatus further comprises a second movable window, the second movable window being movable with respect to the first and second fixed walls, wherein the at least a portion of the first movable window is of a first thickness, and the second movable window has at least a portion of a second thickness, the second thickness being different to the first thickness, wherein the apparatus is operable to cause the at least a portion of the first and the at least a portion of the second movable windows to be selectively located in the test region.

25. The sample testing apparatus of claim 24, wherein, when the at least a portion of the first movable window is located in the test region, an optical path of a first length is defined through the sample in the test region between the first and second fixed walls for electromagnetic radiation introduced through the first fixed window of the first wall, and when the at least a portion of the second movable window is located in the test region, an optical path of a second length is defined through the sample between the first and second fixed walls in the test region for electromagnetic radiation introduced through the first fixed window of the first fixed wall, the first and second path lengths being different.

26. The sample testing apparatus of claim 24, wherein the first and second movable windows are mounted to the same window carrier; optionally wherein the window carrier is movable between at least a first position relative to the fixed walls in which at least a portion of the first movable window is located in the test region and a second position in which at least a portion of the second movable window is located in the test region, and preferably a third position in which no portion of the first or second movable windows is located in the test region.

27. The sample testing apparatus of claim 24, wherein the first and second movable windows are separated from one another by a substrate of a window carrier to which they the first and second moveable windows are mounted.

28. The sample testing apparatus of claim 24, wherein the first and second movable windows are mounted at rotationally different positions on a rotating window carrier, or wherein the first and second movable windows define a rotor rotatable about an axis of rotation.

29. The sample testing apparatus of claim 24, wherein the apparatus is operable to perform a cycle in which the at least a portion of the first and the at least a portion of the second movable window are located sequentially in the test region in any order for performing respective measurements.

30. The sample testing apparatus of claim 1, wherein the apparatus comprises means for causing each movable window to oscillate as it is moved.

31. A sample testing unit comprising the sample testing apparatus of claim 1.

32. The sample testing unit of claim 31, wherein the unit is handheld and portable.

33. The sample testing unit of claim 31, wherein the unit is battery powered.

34. The sample testing unit of claim 31, wherein the transmission cell is located at a distal end of the sample testing unit, the unit optionally having an operator portion at the proximal end thereof arranged to be grasped by a user.

35. The sample testing unit of claim 31, wherein the unit further comprises processing means and a display for outputting data based on measurements performed.

36. A method of using the sample testing apparatus of claim 1 to perform a measurement for use in optical transmission analysis of a fluid sample, the method comprising, in any order, i) providing a fluid sample in the space between the first and second fixed walls, and ii) operating the apparatus to cause the at least a portion of the first movable window to move into the test region;

the method further comprising introducing electromagnetic radiation through the first fixed window associated with the first fixed wall into the transmission cell, wherein the electromagnetic radiation follows the optical path through the sample in the test region comprising a portion extending through the or each gap between a one of the first and second fixed walls and the at least a portion of the first movable window, and detecting the electromagnetic radiation after passing along the path.

37. The method of claim 36, wherein the fluid sample is located in the space before the apparatus is operated to cause the at least a portion of the first movable window to move into the test region.

38. The method of claim 36, further comprising operating the apparatus to cause the at least a portion of the first movable window to move into and out of the test region one or more times while fluid is provided between the first and second fixed walls and without introducing electromagnetic radiation into the transmission cell while the at least a portion of the first movable window is in the test region.

39. The method of claim 36, comprising using the or each measurement obtained in determining the concentration or presence of a substance in the fluid.

40. The method of claim 36, wherein the method comprises using the or each measurement in determining the presence and/or concentration dissolved water in a sample of oil.

41. The method of any claim 36, wherein the method comprises using the or each measurement in determining a total base number (TBN) of a sample of oil.

42. The method of claim 36, wherein the step of providing fluid in the space between the first and second fixed walls comprises immersing the transmission cell of the apparatus in the fluid to be tested so that fluid enters the space.

43. The method of claim 36, wherein the apparatus is used to test a sample of fluid from an extracted sample, wherein the step of providing fluid in the space between the first and second fixed walls comprises dipping the transmission cell into a fluid.

44. The method of claim 36, wherein the apparatus is used for online testing, the step of providing fluid in the space between the first and second fixed walls comprising mounting the apparatus with respect to a system using a fluid to be tested such that the fluid enters the space.

45. The method of claim 36, wherein the first movable window comprises first and second portions of different thickness, the at least a portion of the first movable window being at least a portion of the first portion thereof, wherein the method further comprises operating the apparatus to move at least a portion of the second portion of the first movable window into the test region, and introducing electromagnetic radiation through the first fixed window associated with the first fixed wall into the transmission cell, wherein the electromagnetic radiation follows an optical path through the sample in the test region comprising a portion extending through the or each gap between a one of the first and second fixed walls and the at least a portion of the second portion of the first movable window, and detecting the electromagnetic radiation after passing along the path.

46. The method of claim 36, wherein the apparatus further comprises a second movable window, the method comprising operating the apparatus so that at least a portion of the second movable window moves into the test region, and introducing electromagnetic radiation through the window associated with the first fixed wall into the transmission cell, wherein the electromagnetic radiation follows an optical path through the sample in the test region comprising a portion extending through the or each gap between a one of the first and second fixed walls and the at least a portion of the second movable window, and detecting the electromagnetic radiation after passing along the path.

47. The method of claim 36, wherein when the at least a portion of the first movable window is located in the test region, the optical path defined through the fluid sample is less than 250 micrometres.

48. A method of performing a measurement for use in optical transmission analysis of a fluid sample, the method comprising providing a sample testing apparatus, the apparatus comprising;
a transmission cell comprising first and second walls fixed in a spaced relationship relative to one another to define a space therebetween for receiving a fluid sample in use, at least the first wall being associated with a first fixed window, wherein electromagnetic radiation may be introduced through the first fixed window into the transmission cell in use for detection after passing through the sample;
the apparatus further comprising a first movable window, the first movable window being movable with respect to the first and second fixed walls, wherein the apparatus is operable to cause the first movable window to move with respect to the first and second fixed walls to move at least a portion of the first movable window into and out of a test region of the transmission cell, the test region being a region between the first and second fixed walls in an optical path of electromagnetic radiation introduced through the first fixed window into the transmission cell for passing through a fluid sample located in the space between the first and second fixed walls prior to detection in use;
wherein, when the at least a portion of the first movable window is located in the test region, a gap is defined between the at least a portion of the first movable window and one or both of the first and second fixed walls in the test region of the cell, such that the optical path is defined through a fluid sample in the cell for electromagnetic radiation introduced through the first fixed window associated with the first wall, the optical path through the sample comprising a portion extending through the or each gap between a one of the first and second fixed walls and the at least a portion of the first movable window;
the apparatus further comprising a set of one or more wipers between one or both of the sample fluid contacting surfaces of the first movable window and the first fixed and second fixed walls;
the method comprising;
in any order, i) providing a fluid sample in the space between the first and second fixed walls, and ii) operating the apparatus to cause the at least a portion of the first movable window to move into the test region;
the method further comprising introducing electromagnetic radiation through the first fixed window associated with the first fixed wall into the transmission cell, wherein the electromagnetic radiation follows the optical path through the sample in the test region comprising a portion extending through the or each gap between a one of the first and second fixed walls and the at least a portion of the first movable window, and detecting the electromagnetic radiation after passing along the path; and
the method further comprising the set of one or more wipers wiping one or both of the sample fluid contacting surfaces of the first movable window during relative movement between the first movable window and the first fixed and second fixed walls and/or wiping the sample contacting surface of the or each first fixed window associated with the first and second fixed walls of the apparatus during relative movement between the first movable window and the first and second fixed walls.

49. The method of claim 48, wherein the fluid sample is located in the space before the apparatus is operated to cause the at least a portion of the first movable window to move into the test region.

50. The method of claim 48, further comprising operating the apparatus to cause the at least a portion of the first movable window to move into and out of the test region one or more times while fluid is provided between the first and second fixed walls and without introducing electromagnetic radiation into the transmission cell while the at least a portion of the first movable window is in the test region.

51. The method of claim 48, comprising using the or each measurement obtained in determining the concentration or presence of a substance in the fluid.

52. The method of claim 48, wherein the method comprises using the or each measurement in determining the presence and/or concentration dissolved water in a sample of oil.

53. The method of claim 48, wherein the method comprises using the or each measurement in determining a total base number (TBN) of a sample of oil e.g. engine oil.

54. The method of claim 48, wherein the step of providing fluid in the space between the first and second fixed walls comprises immersing the transmission cell of the apparatus in the fluid to be tested so that fluid enters the space.

55. The method of claim 48, wherein the apparatus is used to test a sample of fluid from an extracted sample, wherein the step of providing fluid in the space between the first and second fixed walls comprises dipping the transmission cell into a fluid.

56. The method of claim 48, wherein the apparatus is used for online testing, the step of providing fluid in the space between the first and second fixed walls comprising mounting the apparatus with respect to a system using a fluid to be tested such that the fluid enters the space.

57. The method of claim 48, wherein the first movable window comprises first and second portions of different thickness, the at least a portion of the first movable window being at least a portion of the first portion thereof, wherein the method further comprises operating the apparatus to move at least a portion of the second portion of the first movable window into the test region, and introducing electromagnetic radiation through the window associated with the first fixed wall into the transmission cell, wherein the electromagnetic radiation follows an optical path through the sample in the test region comprising a portion extending through the or each gap between a one of the first and second fixed walls and the at least a portion of the second portion of the first movable window, and detecting the electromagnetic radiation after passing along the path.

58. The method of claim 48, wherein the apparatus further comprises a second movable window, the method comprising operating the apparatus so that at least a portion of the second movable window moves into the test region, and introducing electromagnetic radiation through the window associated with the first fixed wall into the transmission cell, wherein the electromagnetic radiation follows the optical path through the sample in the test region comprising a portion extending through the or each gap between a one of the first and second fixed walls and the at least a portion of the second movable window, and detecting the electromagnetic radiation after passing along the path.

59. The method of claim 48, wherein when the at least a portion of the first movable window is located in the test region, the optical path defined through the fluid sample is less than 250 micrometres.

60. The method of claim 48, wherein the fluid is engine oil.

61. A sample testing apparatus for use in optical transmission analysis of a fluid sample, the apparatus comprising;
  a transmission cell comprising first and second walls fixed in a spaced relationship relative to one another to define a space therebetween for receiving a fluid sample in use, at least the first wall being associated with a window, wherein electromagnetic radiation may be introduced through the window into the transmission cell in use for detection after passing through the sample;
  the apparatus further comprising a first movable window, the first movable window being movable with respect to the first and second fixed walls, wherein the apparatus is operable to cause the first movable window to move with respect to the first and second fixed walls to move at least a portion of the first movable window into and out of a test region of the transmission cell, the test region being a region between the first and second fixed walls in the optical path of electromagnetic radiation introduced through the first fixed window into the transmission cell for passing through a fluid sample located in the space between the first and second fixed walls prior to detection in use;
  wherein, when the at least a portion of the first movable window is located in the test region, a gap is defined between the at least a portion of the first movable window and one or both of the first and second fixed walls in the test region of the cell, such that an optical path of up to 1000 micrometres is defined through a fluid sample in the cell for electromagnetic radiation introduced through the window associated with the first wall, the optical path through the sample comprising a portion extending through the or each gap between a one of the first and second fixed walls and the at least a portion of the first movable window, and
  the apparatus further comprising a set of one or more wipers for wiping one or both of the sample fluid contacting surfaces of the first movable window during relative movement between the movable window and the first fixed and second fixed walls.

* * * * *